US008524455B2

(12) United States Patent
Chang

(10) Patent No.: US 8,524,455 B2
(45) Date of Patent: Sep. 3, 2013

(54) METHODS AND COMPOSITIONS RELATED TO TR4 LIGAND

(75) Inventor: Chawnshang Chang, Pittsford, NY (US)

(73) Assignee: University of Rochester, Rochester, NY (US)

( * ) Notice: Subject to any disclaimer, the term of this patent is extended or adjusted under 35 U.S.C. 154(b) by 162 days.

(21) Appl. No.: 12/842,569

(22) Filed: Jul. 23, 2010

(65) Prior Publication Data
US 2011/0028538 A1 Feb. 3, 2011

Related U.S. Application Data

(60) Provisional application No. 61/228,537, filed on Jul. 24, 2009, provisional application No. 61/229,223, filed on Jul. 28, 2009.

(51) Int. Cl.
G01N 33/53 (2006.01)
(52) U.S. Cl.
USPC .......................................................... 435/7.1
(58) Field of Classification Search
None
See application file for complete search history.

(56) References Cited

PUBLICATIONS

Zhong et al., 1998, The Journal of Biological Chemistry, 273, 10948-10957.*
Pohlevan et al., Biochim. Biophys. Acta (2009), 1790: 173-181.*
Lin et al., J. Biol. Chem., 2003, 278: 9353-9360.*
Staels et al., Diabetes, 2005, 54: 2460-2470.*
Xie et al., PNAS, 2009, 106: 13353-13358.*
Yan et al., J. Biol. Chem., 1998, 273: 10948-10957.*
Altucci et al., Nature Reviews: Drug Discovery, 2007, 6: 793-810.*
Schmitz et al., Progress in Lipid Research, 2008, 47: 147-155.*
Yang et al., Androgen suppresses PML protein expression in prostate cancer CWR22R cells, Biochem. Biophys. Res. Commun., 314(1):69-75 (2004).
Yki-Jarvinen, Thiazolidinediones, N. Engl J. Med., 351(11):1106-1118 (2004).
Young et al., Induction of the intronic enhancer of the human ciliary neurotrophic factor receptor (CNTFRα) gene by the TR4 orphan receptor. A member of steroid receptor superfamily, J. Biol. Chem., 272(5):3109-3116 (1997).
Zhang et al., Loss of Testicular Orphan Receptor 4 Impairs Normal Myelination in Mouse Forebrain, Mol. Endocrinol., 21(4):908-920 (2007).
Babaev et al., Reduced atherosclerotic lesions in mice deficient for total or macrophage-specific expression of scavenger receptor-A, Arterioscler Thromb. Vasc. Biol., 20(12):2593-2599 (2000).
Barish et al., A Nuclear Receptor Atlas: macrophage activation, Mol. Endocrinol., 19(10):2466-2477 (2005).
Beato et al., Steroid hormone receptors: an update, Hum Reprod Update, 6:225-236 (2000).
Beato, Transcriptional control by nuclear receptors, FASEB, 5:2044-2051 (1991).
Beaven et al., Nuclear receptors in lipidmetabolism: targeting the heart of dyslipidemia, Annu. Rev. Med. 57:313-329 (2006).
Bookout et al., Anatomical profiling of nuclear receptor expression reveals a hierarchical transcriptional network, Cell, 126(4):789-799 (2006).
Castrillo et al., PPARs in atherosclerosis: the clot thickens, J. Clin. Invest., 114(11):1538-1540 (2004).
Chang et al., Human and rat TR4 orphan receptors specify a subclass of the steroid receptor superfamily, Proc. Natl Acad. Sci., 91:6040-6044 (1994).
Chen et al., Deficits in motor coordination with aberrant cerebellar development in mice lacking testicular orphan nuclear receptor 4, Mol. Cell Biol., 25(7):2722-2732 (2005).
Collins et al., Growth retardation and abnormal maternal behavior in mice lacking testicular orphan nuclear receptor 4, Proc. Natl Acad. Sci., 101:15058-15063 (2004).
Endemann et al., CD36 is a receptor for oxidized low density lipoprotein, J. Biol. Chem., 268(16):11811-11816 (1993).
Febbraio et al., Targeted disruption of the class B scavenger receptor CD36 protects against atherosclerotic lesion development in mice, J. Clin. Invest., 105(8):1049-1056 (2000).
Febbraio et al., A null mutation in murine CD36 reveals an important role in fatty acid and lipoproteinmetabolism, J. Biol. Chem., 274(27):19055-19062 (1999).
Forman et al., Hypolipidemic drugs, polyunsaturated fatty acids, and eicosanoids are ligands for peroxisome proliferator-activated receptors α and δ, Proc. Natl Acad. Sci. USA, 94(9):4312-4317 (1997).
Forman et al., 15-Deoxy-Δ 12, 14-prostaglandin J2 is a ligand for the adipocyte determination factor PPARγ, Cell, 83 (5):803-812 (1995).
Glass et al., Atherosclerosis, the road ahead, Cell, 104(4):503-516 (2001).
Joseph et al., LXRs: new therapeutic targets in atherosclerosis?, Curr. Opin. Pharmacol., 3(2):192-197 (2003).
Kim et al., Disruption of TR4 orphan nuclear receptor reduces the expression of liver apolipoprotein E/C-I/C-II gene cluster, J. Biol. Chem., 278(47):46919-46926 (2003).
Kliewer et al., Orphan nuclear receptors: shifting endocrinology into reverse, Science, 284(5415):757-760 (1999).
Kliewer et al., Fatty acids and eicosanoids regulate gene expression through direct interactions with peroxisome proliferator-activated receptors α and γ, Proc. Natl Acad. Sci. USA, 94(9):4318-4323 (1997).
Kliewer et al., A prostaglandin J2 metabolite binds peroxisome proliferatoractivated receptor γ and promotes adipocyte differentiation, Cell, 83(5):813-819 (1995).
Kodama et al., Purification and characterization of a bovine acetyl low density lipoprotein receptor. Proc Natl Acad Sci. USA, 85(23):9238-9242 (1988).
Kunjathoor et al., Scavenger receptors class A-I/II and CD36 are the principal receptors responsible for the uptake of modified low density lipoprotein leading to lipid loading inmacropages, J. Biol. Chem., 277(51):49982-49988 (2002).

(Continued)

Primary Examiner — Ilia Ouspenski
(74) Attorney, Agent, or Firm — Kilpatrick, Townsend & Stockton LLP

(57) ABSTRACT

Disclosed are compositions and methods related to TR4 and aging.

27 Claims, 8 Drawing Sheets

(56) References Cited

PUBLICATIONS

Lee et al., Recent advances in the TR2 and TR4 orphan receptors of the nuclear receptor superfamily. J. Steroid Biochem. Mol. Biol., 81(4-5):291-308 (2002).

Lee et al., Differential regulation of direct repeat 3 vitamin D3 and direct repeat 4 thyroid hormone signaling pathways by the human TR4 orphan receptor, J. Biol. Chem., 274(23):16198-16205 (1999).

Lee et al., Convergence of two repressors through heterodimer formation of androgen receptor and testicular orphan receptor-4: a unique signaling pathway in the steroid receptor superfamily, Proc. Natl Acad. Sci., 96(26):14724-14729 (1999).

Lee et al., Negative feedback control of the retinoid-retinoic acid/retinoid X receptor pathway by the human TR4 orphan receptor, a member of the steroid receptor superfamily, J. Biol. Chem., 273:13437-13443 (1998).

Lehmann et al., An antidiabetic thiazolidinedione is a high affinity ligand for peroxisome proliferator-activated receptor γ (PPAR γ), J. Biol. Chem., 270(22):12953-12956 (1995).

Lehr et al., Immunopathogenesis of atherosclerosis: endotoxin accelerates atherosclerosis in rabbits on hypercholesterolemic diet, Circulation, 104(8):914-920 (2001).

Li et al., Peroxisome proliferator-activated receptor γ ligands inhibit development of atherosclerosis in LDL receptor-deficient mice, J. Clin. Invest., 106(4):523-531 (2000).

Liu et al., Loss of TR4 orphan nuclear receptor reduces phosphoenolpyruvate carboxykinase-mediated gluconeogenesis, Diabetes, 56(12):2901-2909 (2007).

Moore et al., Loss of receptor-mediated lipid uptake via scavenger receptor A or CD36 pathways does not ameliorate atherosclerosis in hyperlipidemic mice, J. Clin. Invest., 115(8):2192-2201 (2005).

Mu et al., Targeted inactivation of testicular nuclear orphan receptor 4 delays and disrupts late meiotic prophase and subsequent meiotic divisions of spermatogenesis, Mol. Cell Biol., 24(13):5887-5899 (2004).

Nagy et al., Oxidized LDL regulates macrophage gene expression through ligand activation of PPARγ, Cell, 93 (2):229-240 (1998).

Nissen et al., Effect of rosiglitazone on the risk of myocardial infarction and death from cardiovascular causes, N. Engl J. Med., 356(24):2457-2471 (2007).

Palinski et al., ApoE-deficient mice are a model of lipoprotein oxidation in atherogenesis. Demonstration of oxidation-specific epitopes in lesions and high titers of autoantibodies to malondialdehyde-lysine in serum, Arterioscler Thromb. Vasc. Biol., 14(4):605-616 (1994).

Rahaman et al., A CD36-dependent signaling cascade is necessary for macrophage foam cell formation, Cell Metab., 4(3):211-221 (2006).

Ricote et al., The peroxisome proliferator-activated receptor-γ is a negative regulator of macrophage activation, Nature, 391(6662):79-82 (1998).

Schote et al., Nuclear receptors in human immune cells: expression and correlations, Mol. Immunol., 44 (6):1436-1445 (2007).

Shyr et al., Modulation of Estrogen Receptor-mediated Transactivation by Orphan Receptor TR4 in MCF-7 Cells, J. Biol. Chem., 277:14622-14628 (2002).

Suzuki et al., A role for macrophage scavenger receptors in atherosclerosis and susceptibility to infection, Nature, 386(6622):292-296 (1997).

Tontonoz et al., PPARγ promotes monocyte/macrophage differentiation and uptake of oxidized LDL, Cell, 93 (2):241-252 (1998).

Tontonoz et al., Regulation of adipocyte gene expression and differentiation by peroxisome proliferator activated receptor γ, Curr. Opin. Genet. Dev., 5(5):571-576 (1995).

Van Berkel et al., Scavenger receptors: friend or foe in atherosclerosis?, Curr. Opin. Lipidol., 16(5):525-535 (2005).

Wang et al., Apolipoprotein secretion and lipid synthesis: regulation by fatty acids in newborn swine intestinal epithelial cells, Am. J. Physiol., 272(5 Pt 1):G935-942 (1997).

Witztum, You are right too!, J. Clin. Invest., 115(8):2072-2075 (2005).

Xie et al., Regulation of interleukin-6-mediated PI3K activation and neuroendocrine differentiation by androgen signaling in prostate cancer LNCaP cells, Prostate, 60(1):61-67 (2004).

Xu et al., Molecular recognition of fatty acids by peroxisome proliferator-activated receptors, Mol. Cell, 3(3):397-403 (1999).

Yang et al., Nuclear receptor expression links the circadian clock to metabolism, Cell, 126(4):801-810 (2006).

Yang et al., Induction of androgen receptor expression by phosphatidylinositol 3-kinase/Akt downstream substrate, FOXO3a, and their roles in apoptosis of LNCaP prostate cancer cells, J. Biol. Chem., 280(39):33558-33565 (2005).

* cited by examiner

SEQUENCE LISTING

<160> NUMBER OF SEQ ID NOS: 14

<210> SEQ ID NO 1
<211> LENGTH: 615
<212> TYPE: PRT
<213> ORGANISM: Homo sapiens
<220> FEATURE:
<221> NAME/KEY: UNSURE
<222> LOCATION: (1)..(615)
<223> OTHER INFORMATION: Protein id NP_003289

<400> SEQUENCE: 1

```
Met Thr Ser Pro Ser Pro Arg Ile Gln Ile Ile Ser Thr Asp Ser Ala
1               5                   10                  15

Val Ala Ser Pro Gln Arg Ile Gln Gly Ser Glu Pro Ala Ser Gly Pro
            20                  25                  30

Leu Ser Val Phe Thr Ser Leu Asn Lys Glu Lys Ile Val Thr Asp Gln
        35                  40                  45

Gln Thr Gly Gln Lys Ile Gln Ile Val Thr Ala Val Asp Ala Ser Gly
    50                  55                  60

Ser Pro Lys Gln Gln Phe Ile Leu Thr Ser Pro Asp Gly Ala Gly Thr
65                  70                  75                  80

Gly Lys Val Ile Leu Ala Ser Pro Glu Thr Ser Ser Ala Lys Gln Leu
                85                  90                  95

Ile Phe Thr Thr Ser Asp Asn Leu Val Pro Gly Arg Ile Gln Ile Val
            100                 105                 110

Thr Asp Ser Ala Ser Val Glu Arg Leu Leu Gly Lys Thr Asp Val Gln
        115                 120                 125

Arg Pro Gln Val Val Glu Tyr Cys Val Val Cys Gly Asp Lys Ala Ser
    130                 135                 140

Gly Arg His Tyr Gly Ala Val Ser Cys Glu Gly Cys Lys Gly Phe Phe
145                 150                 155                 160

Lys Arg Ser Val Arg Lys Asn Leu Thr Tyr Ser Cys Arg Ser Asn Gln
                165                 170                 175

Asp Cys Ile Ile Asn Lys His His Arg Asn Arg Cys Gln Phe Cys Arg
            180                 185                 190

Leu Lys Lys Cys Leu Glu Met Gly Met Lys Met Glu Ser Val Gln Ser
        195                 200                 205

Glu Arg Lys Pro Phe Asp Val Gln Arg Glu Lys Pro Ser Asn Cys Ala
    210                 215                 220

Ala Ser Thr Glu Lys Ile Tyr Ile Arg Lys Asp Leu Arg Ser Pro Leu
225                 230                 235                 240

Ile Ala Thr Pro Thr Phe Val Ala Asp Lys Asp Gly Ala Arg Gln Thr
                245                 250                 255

Gly Leu Leu Asp Pro Gly Met Leu Val Asn Ile Gln Gln Pro Leu Ile
            260                 265                 270

Arg Glu Asp Gly Thr Val Leu Leu Ala Thr Asp Ser Lys Ala Glu Thr
        275                 280                 285

Ser Gln Gly Ala Leu Gly Thr Leu Ala Asn Val Val Thr Ser Leu Ala
    290                 295                 300

Asn Leu Ser Glu Ser Leu Asn Asn Gly Asp Thr Ser Glu Ile Gln Pro
305                 310                 315                 320

Glu Asp Gln Ser Ala Ser Glu Ile Thr Arg Ala Phe Asp Thr Leu Ala
                325                 330                 335

Lys Ala Leu Asn Thr Thr Asp Ser Ser Ser Ser Pro Ser Leu Ala Asp
```

340                 345                 350
Gly Ile Asp Thr Ser Gly Gly Ser Ile His Val Ile Ser Arg Asp
            355                 360                 365

Gln Ser Thr Pro Ile Ile Glu Val Glu Gly Pro Leu Leu Ser Asp Thr
370                 375                 380

His Val Thr Phe Lys Leu Thr Met Pro Ser Pro Met Pro Glu Tyr Leu
385                 390                 395                 400

Asn Val His Tyr Ile Cys Glu Ser Ala Ser Arg Leu Leu Phe Leu Ser
                405                 410                 415

Met His Trp Ala Arg Ser Ile Pro Ala Phe Gln Ala Leu Gly Gln Asp
            420                 425                 430

Cys Asn Thr Ser Leu Val Arg Ala Cys Trp Asn Glu Leu Phe Thr Leu
        435                 440                 445

Gly Leu Ala Gln Cys Ala Gln Val Met Ser Leu Ser Thr Ile Leu Ala
    450                 455                 460

Ala Ile Val Asn His Leu Gln Asn Ser Ile Gln Glu Asp Lys Leu Ser
465                 470                 475                 480

Gly Asp Arg Ile Lys Gln Val Met Glu His Ile Trp Lys Leu Gln Glu
                485                 490                 495

Phe Cys Asn Ser Met Ala Lys Leu Asp Ile Asp Gly Tyr Glu Tyr Ala
            500                 505                 510

Tyr Leu Lys Ala Ile Val Leu Phe Ser Pro Asp His Pro Gly Leu Thr
        515                 520                 525

Ser Thr Ser Gln Ile Glu Lys Phe Gln Glu Lys Ala Gln Met Glu Leu
    530                 535                 540

Gln Asp Tyr Val Gln Lys Thr Tyr Ser Glu Asp Thr Tyr Arg Leu Ala
545                 550                 555                 560

Arg Ile Leu Val Arg Leu Pro Ala Leu Arg Leu Met Ser Ser Asn Ile
                565                 570                 575

Thr Glu Glu Leu Phe Phe Thr Gly Leu Ile Gly Asn Val Ser Ile Asp
            580                 585                 590

Ser Ile Ile Pro Tyr Ile Leu Lys Met Glu Thr Ala Glu Tyr Asn Gly
        595                 600                 605

Gln Ile Thr Gly Ala Ser Leu
    610                 615

<210> SEQ ID NO 2
<211> LENGTH: 8330
<212> TYPE: DNA
<213> ORGANISM: Homo sapiens
<220> FEATURE:
<221> NAME/KEY: misc_feature
<222> LOCATION: (1)..(8330)

<400> SEQUENCE: 2
ccgctcccac ctcggcgtct cgtctctcgc ccgctgcccc gcgagcccgc ggccccgggg    60
ctcccgccat ccgccgacac cgggagcccg ggctccccgc gccctgccct ccgcgccggg   120
ggccgcccgc cgcagacacg ggacccgctt cgaggccgct ttggcgccaa atcctgaggt   180
aacacgtaca cagacctctc ggccggaatc tccagggatg accagcccct ccccacgcat   240
ccagataatc tccaccgact ctgctgtagc ctcacctcag cgcattcagg gctctgaacc   300
tgcctctggc ccattgagtg ttttcacatc tttgaacaaa gagaagattg tcacagacca   360
gcagacagga cagaaaatcc agatagtcac cgcagtggac cgctccggat cccccaaaca   420
gcagttcatc ctgaccagcc cagatggagc tggaactggg aaggtgatcc tggcttcccc   480

```
agagacatcc agcgccaagc aactcatatt caccacctca gacaacctcg tccctggcag      540
gatccagatt gtcacggatt ctgcctctgt ggagcgttta ctggggaaga cggacgtcca      600
gcggccccag gtggtagagt actgtgtggt ctgtggcgac aaagcctccg gccgtcacta      660
tggggctgtc agttgtgaag gttgcaaagg tttcttcaaa aggagtgtga ggaaaaattt      720
gacctacagc tgccggagca accaagactg catcatcaat aaacatcacc ggaaccgctg      780
tcagttttgc cggctgaaaa aatgcttaga gatgggcatg aaaatggaat ctgtgcagag      840
tgaacggaag cccttcgatg tgcaacggga gaaaccaagc aattgtgctg cttcaactga      900
gaaaatctat atccggaaag acctgagaag tccctgata gctactccca cgtttgtggc       960
agacaaagat ggagcaagac aaacaggtct tcttgatcca gggatgcttg tgaacatcca     1020
gcagcctttg atacgtgagg atggtacagt tctcctggcc acggattcta aggctgaaac     1080
aagccaggga gctctgggca cactggcaaa tgtagtgacc tcccttgcca acctaagtga     1140
atctttgaac aacggtgaca cttcagaaat ccagccagag gaccagtctg caagtgagat     1200
aactcgggca tttgatacct tagctaaagc acttaatacc acagacagct cctcttctcc     1260
aagcttggca gatgggatag acaccagtgg aggaggagc atccacgtca tcagcagaga     1320
ccagtcgaca cccatcattg aggttgaagg ccccctcctt tcagacacac acgtcacatt     1380
taagctaaca atgcccagtc caatgccaga gtacctcaac gtgcactaca tctgtgagtc     1440
tgcatcccgt ctgcttttcc tctcaatgca ctgggctcgg tcaatcccag cctttcaggc     1500
acttgggcag gactgcaaca ccagccttgt gcgggcctgc tggaatgagc tcttcacccct    1560 cggcctggcc cagtgtgccc aggtcatgag tctctccacc atcctggctg ccattgtcaa     1620
ccacctgcag aacagcatcc aggaagataa actttctggt gaccggataa agcaagtcat     1680
ggagcacatc tggaagctgc aggagttctg taacagcatg gcgaagctgg atatagatgg     1740
ctatgagtat gcatacctta aagctatagt tctctttagc cccgatcatc caggtttgac     1800
cagcacaagc cagattgaaa aattccaaga aaaggcacag atggagttgc aggactatgt     1860
tcagaaaacc tactcagaag acacctaccg attggcccgg atcctcgttc gcctgccggc     1920
actcaggctg atgagctcca acataacaga agaacttttt tttactggtc tcattggcaa     1980
tgtttcgata gacagcataa tcccctacat cctcaagatg gagacagcag agtataatgg     2040
ccagatcacc ggagccagtc tatagcgcaa accacacacc tgccaaggag caacagaatc     2100
cttccaggac cgttcacata caaagaaaag tagtggtatt ttggtatgtg caaatatttc     2160
catatgttag ccatttcctg tctggtttct ccttatctgt taatcccaga caatagcaat     2220
taaaagacta gtaggatcct ttcctgacat aagaaatgtt ttaatgcctt tgatgaagc      2280 agcagatttt ggaacaatct tttaactcaa tttgtattta gaaattctca aagggcaaaa     2340
aacaaaaaaa aaggttttat aatgtcagag actagtatta agaaaactg aaagaacctg      2400 agagaatagt atgtgtgtat atatatatat aaaaaagtcc ttggaattat agatactaat     2460
taccagggta ataatattag cactttctaa gcacttatca atgtgtaacg ttagcaacat     2520
cttgcctgtg ggcagggcaa atggaaaact gtgtatgtct tttgccgaaa tgctaatgat     2580
ttctgtgaaa actcactagg gtacaggaga caatcattta tgtttaagaa aagaaggcat     2640
cattcctaat tgtgtgcaca tgttgtggag ttgagctgaa ttctgtgaat ggaaacgtgg     2700
ctcatttgca tcatgcagta agtgggagtg tggtagcaca gtcggtggtg acccagttca     2760
gaagcttcta gccatagagc agacacttgt caggttccct gactacttgg tcctggtctc     2820
tgatgggcat ctgcagactc ctctagaacc tggggttctc ctttgatgac tggttatctg     2880
```

```
aattggattg caactagtca gacattaact gccaaatgag atgtacagtt cctccagcaa   2940
gtgaaaacat ccccaagtca catccgccgc tcgtggcaga tggagccttg tgaccaaaaa   3000
gtgcaaggtg ggcattttga gctcttgaca gtacttccaa tacaattggg ggtgcttgtg   3060
tgtttgtcca gatggaggag tgtggccttg gagtgtgagc gttaccttcc cagggctttc   3120
cactccaaat gccccttga aaagggctcg tgtttctgca gctccatcat aactgtgagg    3180
ctggattggg gctgggcagg agcctgctgc cgcctggcga gagtggttag ggcctggtaa   3240
agctggatgg aaggtttcag gacaatttct tcctgttgac cttaaatacc agagatttta   3300
aaaatgtgta tagactcagc atctctgttg gcaagtctgt taatgttacc agcacactgt   3360
gcactttggt tcccccaggt gtgtgccagc cgaccacccc ggagcatttt aaatgcaggc   3420
tgcttgctcc ttaaaaacaa ccctcaattt ccagggtgat agtctttctc ctcataaatt   3480
gtagcaacca gagtttacag caagaacagt atgcgcttaa aaggaagtta tgtctaactt   3540
caaacacccg taaattccca cggatgtgaa tatatagcaa gcttttcctg tttgagaaca   3600
gtggcatgtg aagacccgg tcaattgctt tgtcttttgc ttttttaaata gtccagatta   3660
agaaaataca ccctgttggg ttaaatttgc ctctcttgat ttgttaatca gatgatatcc   3720
aaaaagatcc ctggacactc ccctgactca caggtgctct gatctggctc aggctggcgc   3780
cacatgtgct ccacagggt gcagtctggc cagctacaga cgcccctgtg gtgccacatt    3840
ggacagaatg gaagctgctg caggctcaag gcagaacagg atgcttgatc ctgaagggtt   3900
agcagcactt tacgcaagtc agtgttagta gggtaagtgg gaacagtgtt tccaacttct   3960
aaattcttgt ttggatttaa ttatatcatt ttataattct tgccttggca gcaaattttg   4020
gagagtagtg ggagtggcca ttataaaatg atggaaagga tttaattttg ccagcttaaa   4080
gtaatttta cttttctaac cctgatgtgt tttcagtttc aaaattaaga caaaaaacca    4140
gctgagacaa tggaattagg gcaggtttgt ttcatttctg cttgtgaagg cttttagtag   4200
caggcatcct gcagctcagt ggtgcctcta acacagattg ttgcctgcct tccgtcgttt   4260
tgatccttga gagtgaccat gagggccatg ttgcagttcc ctgggaatac aagcataaca   4320
gctttcagat cccagttctt ggtgttggtg aaaaggtctc caccagcccc tcctctcatt   4380
cccaggtcat tcagtggcag ccagtaggct gcttagactc aggctggata aggaagtgtt   4440
gggctgtggt gaaacaacct tgcagaaaac gtgattttgc ttggaaaggt gctgattcta   4500
acctggtcct gctctttaag tccccttgct ggtgatggct gattccaggg actgttttgg   4560
gctttgaaca cctcttggtt ggtttctgag atcctcttgg ccttactttg aagtggcctt   4620
ttctttaagg atcatgtcca cgtaacctgt attcttgctg ctttaactca tttcaagcct   4680
ctgactgcag gtccatttca tctcctgtca ggttggttaa gtaaagtcag cccaaagtca   4740
agaattactt aaagagatgc aaaccaaata tttgggctcc aactttcaca gggcttatag   4800
cccttattag cagtttgtga aactttgggt ttcatgaagt gagacctgtc ctctggctac   4860
tgaactccat ggagccacgt tcatgctccc tcttctactg gcctggctgc tcctccctca   4920
atgaggagag gcagctggct cagagaggtg ggacagacac atgctgtcat cagttaagtg   4980
agctcttttc cagaagtatc tcagataatg ttgggttaag acagatagat gttgaaaatg   5040
gtggagatca ttcacacatta gcataaaaca ggacaggaag agatttttg aaagaccaaa    5100
ttagttgagc aagtaatact tttcaagtta ctcctggaag gtgtttttaa ggaagtgtgt   5160
tacctaccat actctcctaa tttgacattt ctgtgtcctg aggagttaca tttattgtct   5220
aaccccttgcc ataaggctgt ggtttgaggt tcttttgctg ttctgggctt tatatttaat  5280
```

```
ttcaggtgta gtcacttcta agatgtgtaa ttgccctcaa gagggactga ttttagctt      5340 gtcattgtca gtattgaatg tggactcttc tgaggcagtt aggacaccag ccatggtgtt      5400
aacagtggat gcgttaggct ccttaatctc aaggcaatat ccacgctaca cacatactta      5460
ttagctgtct tacttgtttg ggggatagtt acggcaagga gcaaaaaatt ctaaggactc      5520
tagctgtttc tagtgctttt actttcatag tcctttgagg acatttcctg cagagcactc      5580
ttgctcacag cccgccctct gcagggcttc cagcccctgg ccgcaatcag cagttcatgc      5640
cacatgtgta catccatgtt ctgggacctg atctcattgg agtccagaag cttgttgccc      5700
actttccagt gtaaatgact ttatgtgcaa tggggtcata ggtaacattt taactctttt      5760
cttagtccag gtcataggaa gtctcatcat ctgacagcca cttttctccc agggaaggcg      5820
gtgcccactg ggccctggga atgcctgagc cagcagagca gatgcccac gtgcttcctt      5880 tatccagctt ccattctctc agttatgagg ctctttgaaa atgtcttaac tttgatgtaa      5940 attttaaag ccaccccctc atcaagacag gttggtttg ggtcttttgt acacagggtc       6000
tggaccttct cattgtgtgc ctcccaccag cgtgcacttc gtatgtccag ccctgggtcc      6060
cttcagcagc attgtgcgtg tacaggttc taggctgtaa gactgaatga atgtacatgt       6120
gtttatatcc tctccatatg tacagtgtat atagtgtgtg tatgtgtaca tagatgtata      6180
ttatgtatac agacatgtat ccaaactttc ctttaaagag agttttcat aaagttgcta       6240 atgtaaactg atatgggtgt tccaaggtcc ctcggcaggg aagatttgct ggtgattttc      6300
ttcactccat tttcctttgg gtgagcctgc ctgggaaggg ccatgaagtc agaatctcca      6360
ctctgcaaaa ggaagaattc caggcagaag aggttctgac agggtgacat ttccgtatat      6420
tctctaggtt cggacaagag ccaggaagct ggaagacagt ttatcttaat atccaaaact      6480
aagtgggaat ttttaaccttt tcatgcacc tattcatggc cctacctgga aggaacttgg        6540
cagttgggtt gagccatcag ccttcccagc tattcagctc tgttgagtag cccagagaca      6600
ggcgtcacgg tcagagattc agaacggtct gtgtcagtga ggcctgactc ccaaagatgg      6660
tagcaatttc ccaggcttgc gctgtgctca gtcagcaaga tgtggggcac tgtcctatga      6720
ctgaataaat agtaattccc atcttctat cgccagttaa aaataaacaa cctaccaagt       6780
attattcttt aaaactaagc atggatgttg atggctaact tctgcggcat ataagctaca      6840
gatctcaagt tacttctcta actgtaagca tgtaaatgac tttaactcct ttctataagt      6900
tatgatttta aattttcaga taagaattgc attttaatat ggatatgtgt gcccttaaaa      6960
gctacagata ccaaattttc ctcgtccagg tctactcgga cgaattttcc cccttaatct      7020
ggccttaaac tgagactcgg cccttgagag ccagggcctg cccagcagt agttgctcat       7080 agacctggga agcaggggcc tgctggaagg aatcactaga ttgctgcaaa aactcacata      7140
atccacagtt tcctcttttt cttttaaaa taagttatca aaatgtttta aaaacactt       7200 atgagaccat agtactcagt gccttttgtg agacagtggg tcatttagcc ttcagcttcc      7260 ctgttttga tgtagagaaa gcttctattt cactggcctc atcccacaag attgtgcgac       7320 cttcccgt catagcctgt cgtgacaatc acgctattga agtggctttt ctagttaaaa       7380
tgcaattgga aacttgacag tctctaaatg aattaaaagt ttcctttggg gctatttagc      7440
ttaacagcag tctacaaata attaaagtgt gagcttaaga aaagtatctt tgcggggaga      7500
aaaatgtcag atatttttaa tgcccagcta taaataattt tggtgtcttg atatttatac      7560
atgcaaaata gaaaaaaaat gttcaacatt tattgattga tagactgtta aaatttaatg      7620
tttggaataa catttggaag tagtagactt tgcattaaaa aatggctttt ctttaggaaa      7680
```

```
gtataatcaa ttattttaat gaccatagca ttcatggact caaatgctgc tgccacacac    7740
aactcaagtg ctggaatatt tttctacagt ctctctgttc tacggattat cttgtaaacc    7800
agtgttcaac tagttttata actgaaaagc tgcacatttt tcacagtaca agccgtagtt    7860
tttacctgta gtttggactt ctctgttaga atgtaactgc attaccagcc cttttaaagg    7920
catctatcta tcaaaggaaa atttgggtgt tagattttct tgggaccgtt tctgtaacct    7980
ttgcccttca caatatagaa aatattggtt ttgccattac attttaatgc caggtttaaa    8040
acctgttgaa agctgcagct ttatacagct ttcttctccc tgtgaaatca ctttgtttat    8100
gtgatggcat ttaaaaaata gcatgttctt tttaaactga attttatatc taatcaatgt    8160
cttcagtctt gaagaagaat ttgcattgtt gtgtttgtat atagagtatt gcagtgcatg    8220
aattagcttt atgcatttta ttaaatgctg tttcaatgtg gcattattgt tgtggcttaa    8280
tactactacc taaatgaggt ttatactatt aaaagtgaat taaagactaa              8330

<210> SEQ ID NO 3
<211> LENGTH: 477
<212> TYPE: PRT
<213> ORGANISM: Homo sapiens
<220> FEATURE:
<221> NAME/KEY: UNSURE
<222> LOCATION: (1)..(477)
<223> OTHER INFORMATION: Protein id  NP_619726

<400> SEQUENCE: 3

Met Thr Met Val Asp Thr Glu Met Pro Phe Trp Pro Thr Asn Phe Gly
1               5                   10                  15

Ile Ser Ser Val Asp Leu Ser Val Met Glu Asp His Ser His Ser Phe
            20                  25                  30

Asp Ile Lys Pro Phe Thr Thr Val Asp Phe Ser Ser Ile Ser Thr Pro
        35                  40                  45

His Tyr Glu Asp Ile Pro Phe Thr Arg Thr Asp Pro Val Val Ala Asp
    50                  55                  60

Tyr Lys Tyr Asp Leu Lys Leu Gln Glu Tyr Gln Ser Ala Ile Lys Val
65                  70                  75                  80

Glu Pro Ala Ser Pro Pro Tyr Tyr Ser Glu Lys Thr Gln Leu Tyr Asn
                85                  90                  95

Lys Pro His Glu Glu Pro Ser Asn Ser Leu Met Ala Ile Glu Cys Arg
            100                 105                 110

Val Cys Gly Asp Lys Ala Ser Gly Phe His Tyr Gly Val His Ala Cys
        115                 120                 125

Glu Gly Cys Lys Gly Phe Phe Arg Arg Thr Ile Arg Leu Lys Leu Ile
    130                 135                 140

Tyr Asp Arg Cys Asp Leu Asn Cys Arg Ile His Lys Lys Ser Arg Asn
145                 150                 155                 160

Lys Cys Gln Tyr Cys Arg Phe Gln Lys Cys Leu Ala Val Gly Met Ser
                165                 170                 175

His Asn Ala Ile Arg Phe Gly Arg Met Pro Gln Ala Glu Lys Glu Lys
            180                 185                 190

Leu Leu Ala Glu Ile Ser Ser Asp Ile Asp Gln Leu Asn Pro Glu Ser
        195                 200                 205

Ala Asp Leu Arg Ala Leu Ala Lys His Leu Tyr Asp Ser Tyr Ile Lys
    210                 215                 220

Ser Phe Pro Leu Thr Lys Ala Lys Ala Arg Ala Ile Leu Thr Gly Lys
225                 230                 235                 240

Thr Thr Asp Lys Ser Pro Phe Val Ile Tyr Asp Met Asn Ser Leu Met
```

```
                    245                 250                 255
Met Gly Glu Asp Lys Ile Lys Phe Lys His Ile Thr Pro Leu Gln Glu
                260                 265                 270

Gln Ser Lys Glu Val Ala Ile Arg Ile Phe Gln Gly Cys Gln Phe Arg
            275                 280                 285

Ser Val Glu Ala Val Gln Glu Ile Thr Glu Tyr Ala Lys Ser Ile Pro
        290                 295                 300

Gly Phe Val Asn Leu Asp Leu Asn Asp Gln Val Thr Leu Leu Lys Tyr
305                 310                 315                 320

Gly Val His Glu Ile Ile Tyr Thr Met Leu Ala Ser Leu Met Asn Lys
                325                 330                 335

Asp Gly Val Leu Ile Ser Glu Gly Gln Gly Phe Met Thr Arg Glu Phe
            340                 345                 350

Leu Lys Ser Leu Arg Lys Pro Phe Gly Asp Phe Met Glu Pro Lys Phe
        355                 360                 365

Glu Phe Ala Val Lys Phe Asn Ala Leu Glu Leu Asp Asp Ser Asp Leu
    370                 375                 380

Ala Ile Phe Ile Ala Val Ile Ile Leu Ser Gly Asp Arg Pro Gly Leu
385                 390                 395                 400

Leu Asn Val Lys Pro Ile Glu Asp Ile Gln Asp Asn Leu Leu Gln Ala
                405                 410                 415

Leu Glu Leu Gln Leu Lys Leu Asn His Pro Glu Ser Ser Gln Leu Phe
            420                 425                 430

Ala Lys Leu Leu Gln Lys Met Thr Asp Leu Arg Gln Ile Val Thr Glu
        435                 440                 445

His Val Gln Leu Leu Gln Val Ile Lys Lys Thr Glu Thr Asp Met Ser
    450                 455                 460

Leu His Pro Leu Leu Gln Glu Ile Tyr Lys Asp Leu Tyr
465                 470                 475

<210> SEQ ID NO 4
<211> LENGTH: 1892
<212> TYPE: DNA
<213> ORGANISM: Homo sapiens
<220> FEATURE:
<221> NAME/KEY: Unsure
<222> LOCATION: (1)..(1892)
<223> OTHER INFORMATION: Gene id  NM_138712

<400> SEQUENCE: 4
ggcgcccgcg cccgccccg cgccgggccc ggctcggccc gacccggctc cgccgcgggc      60
aggcggggcc cagcgcactc ggagcccgag cccgagccgc agccgccgcc tggggcgctt    120
gggtcggcct cgaggacacc ggagaggggc gccacgccgc cgtggccgca gatttgaaag    180
aagccaacac taaaccacaa atatacaaca aggccatttt ctcaaacgag agtcagcctt    240
taacgaaatg accatggttg acacagagat gccattctgg cccaccaact ttgggatcag    300
ctccgtggat ctctccgtaa tggaagacca ctcccactcc tttgatatca gcccttcac     360 tactgttgac ttctccagca tttctactcc acattacgaa gacattccat tcacaagaac    420
agatccagtg gttgcagatt acaagtatga cctgaaactt caagagtacc aaagtgcaat    480
caaagtggag cctgcatctc caccttatta ttctgagaag actcagctct acaataagcc    540
tcatgaagag ccttccaact ccctcatggc aattgaatgt cgtgtctgtg agataaagc     600 ttctggattt cactatggag ttcatgcttg tgaaggatgc aagggtttct tccgagaac     660 aatcagattg aagcttatct atgacagatg tgatcttaac tgtcggatcc acaaaaaaag    720
```

```
tagaaataaa tgtcagtact gtcggtttca gaaatgcctt gcagtgggga tgtctcataa      780
tgccatcagg tttgggcgga tgccacaggc cgagaaggag aagctgttgg cggagatctc      840
cagtgatatc gaccagctga atccagagtc cgctgacctc cgggccctgg caaaacattt      900
gtatgactca tacataaagt ccttcccgct gaccaaagca aaggcgaggg cgatcttgac      960
aggaaagaca acagacaaat caccattcgt tatctatgac atgaattcct taatgatggg     1020
agaagataaa atcaagttca acacatcac cccctgcag gagcagagca aagaggtggc      1080
catccgcatc tttcagggct gccagtttcg ctccgtggag gctgtgcagg agatcacaga     1140
gtatgccaaa agcattcctg gttttgtaaa tcttgacttg aacgaccaag taactctcct     1200
caaatatgga gtccacgaga tcatttacac aatgctggcc tccttgatga ataaagatgg     1260
ggttctcata tccgagggcc aaggcttcat gacaaggggg tttctaaaga gcctgcgaaa     1320 gcctttggt gactttatgg agcccaagtt tgagtttgct gtgaagttca atgcactgga      1380
attagatgac agcgacttgg caatatttat tgctgtcatt attctcagtg agaccgccc      1440 aggtttgctg aatgtgaagc ccattgaaga cattcaagac aacctgctac aagccctgga     1500
gctccagctg aagctgaacc accctgagtc ctcacagctg tttgccaagc tgctccagaa     1560
aatgacagac ctcagacaga ttgtcacgga acacgtgcag ctactgcagg tgatcaagaa     1620
gacggagaca gacatgagtc ttcacccgct cctgcaggag atctacaagg acttgtacta     1680
gcagagagtc ctgagccact gccaacattt cccttcttcc agttgcacta ttctgaggga     1740
aaatctgaca cctaagaaat ttactgtgaa aagcattttt aaaagaaaa ggttttagaa      1800 tatgatctat tttatgcata ttgtttataa agacacattt acaatttact tttaatatta     1860
aaaattacca tattatgaaa ttgctgatag ta                                   1892
```

<210> SEQ ID NO 5
<211> LENGTH: 28
<212> TYPE: PRT
<213> ORGANISM: Homo sapiens
<220> FEATURE:
<221> NAME/KEY: MISC_FEATURE
<222> LOCATION: (1)..(28)
<223> OTHER INFORMATION: N-terminal end of PPARgamma variant 2 (protein
      id NP_056953)

<400> SEQUENCE: 5

Met Gly Glu Thr Leu Gly Asp Ser Pro Ile Asp Pro Glu Ser Asp Ser
1               5                   10                  15

Phe Thr Asp Thr Leu Ser Ala Asn Ile Ser Gln Glu
            20                  25

<210> SEQ ID NO 6
<211> LENGTH: 13
<212> TYPE: DNA
<213> ORGANISM: Artificial Sequence
<220> FEATURE:
<223> OTHER INFORMATION: chemically synthesized; TR4 response element
<220> FEATURE:
<221> NAME/KEY: misc_feature
<222> LOCATION: (1)..(13)

<400> SEQUENCE: 6
tggcctctga ctt                                                          13

<210> SEQ ID NO 7
<211> LENGTH: 12
<212> TYPE: DNA
<213> ORGANISM: Artificial Sequence
<220> FEATURE:

```
<223> OTHER INFORMATION: chemically synthesized; mutant TR4 response
      element
<220> FEATURE:
<221> NAME/KEY: misc_feature
<222> LOCATION: (1)..(12)

<400> SEQUENCE: 7
tgaaactgac tt                                                            12

<210> SEQ ID NO 8
<211> LENGTH: 19
<212> TYPE: DNA
<213> ORGANISM: Unknown
<220> FEATURE:
<223> OTHER INFORMATION: chemically synthesized;
<220> FEATURE:
<221> NAME/KEY: misc_feature
<222> LOCATION: (1)..(19)

<400> SEQUENCE: 8
cgggagaaac caagcaatt                                                     19

<210> SEQ ID NO 9
<211> LENGTH: 19
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(19)

<400> SEQUENCE: 9
gttctccgaa cgtgtcacg                                                     19

<210> SEQ ID NO 10
<211> LENGTH: 13
<212> TYPE: DNA
<213> ORGANISM: Artificial Sequence
<220> FEATURE:
<223> OTHER INFORMATION: chemically synthesized; PPAR response element
<220> FEATURE:
<221> NAME/KEY: misc_feature
<222> LOCATION: (1)..(13)
<223> OTHER INFORMATION: n can be any nucleotide and can be a variety of
      lengths

<400> SEQUENCE: 10
tgacctntga cct                                                           13

<210> SEQ ID NO 11
<211> LENGTH: 13
<212> TYPE: DNA
<213> ORGANISM: Artificial Sequence
<220> FEATURE:
<223> OTHER INFORMATION: chemically synthesized; PPAR response element
<220> FEATURE:
<221> NAME/KEY: misc_feature
<222> LOCATION: (1)..(13)
<223> OTHER INFORMATION: n can be any nucleotide and can be a variety of
      lengths

<400> SEQUENCE: 11
aggtcanagg tca                                                           13

<210> SEQ ID NO 12
<211> LENGTH: 13
<212> TYPE: DNA
<213> ORGANISM: Artificial Sequence
<220> FEATURE:
```

```
-continued

<223> OTHER INFORMATION: chemically synthesized; TR4 response element
<220> FEATURE:
<221> NAME/KEY: misc_feature
<222> LOCATION: (1)..(13)
<223> OTHER INFORMATION: n can be any nucleotide and a variety of
      lengths

<400> SEQUENCE: 12
aggtcanagg tca                                                          13

<210> SEQ ID NO 13
<211> LENGTH: 24
<212> TYPE: DNA
<213> ORGANISM: Artificial Sequence
<220> FEATURE:
<223> OTHER INFORMATION: chemically synthesized; FLAG tag
<220> FEATURE:
<221> NAME/KEY: misc_feature
<222> LOCATION: (1)..(24)

<400> SEQUENCE: 13
gactacaaag acgatgacga caag                                              24

<210> SEQ ID NO 14
<211> LENGTH: 47
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(47)

<400> SEQUENCE: 14
cgggagaaac caagcaattt ctcttgaaaa ttgcttggtt tctcccg                     47
```

METHODS AND COMPOSITIONS RELATED TO TR4 LIGAND

CROSS-REFERENCE TO THE RELATED APPLICATIONS

This application claims benefit of U.S. Provisional Application No. 61/229,223, filed Jul. 28, 2009 and U.S. Provisional Application No. 61/228,537, filed Jul. 24, 2009. U.S. Provisional Application No. 61/229,223, filed Jul. 28, 2009 and U.S. Provisional Application No. 61/228,537, filed Jul. 24, 2009 are hereby incorporated herein by reference in their entirety.

STATEMENT REGARDING FEDERALLY SPONSORED RESEARCH

This application was supported by NIH Grants DK73414 and George Whipple Professorship endowment. The Government has certain rights to this invention.

REFERENCE TO SEQUENCE LISTING

The Sequence Listing submitted Oct. 6, 2010 as a text file named "24376_43_8403_2010_10_06_AMD_AFD_Sequence_Listing_text_file.txt," created on Sep. 16, 2010, and having a size of 26,428 bytes is hereby incorporated by reference pursuant to 37 C.F.R. §1.52(e)(5).

SUMMARY

In accordance with the purposes of this invention, as embodied and broadly described herein, the disclosed compositions and methods, in one aspect, relate to TR4 ligand and the relationship between the TR4 receptor and the PPAR receptor.

It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several embodiments.

(FIG. 1A) Foam cell formation is decreased in $TR4^{-/-}$ macrophages. Thioglycolate-stimulated peritoneal macrophages from $TR4^{+/+}$ mice and $TR4^{-/-}$ mice were seeded on 96-well plates and exposed to 100 g/ml oxLDL for 24 h. Cells were then fixed with 3.7% formaldehyde and stained with 0.5% Oil Red O. Cells containing Oil-Red O-positive fat droplets were considered foam cells. Data shown from two pairs of mice represent results from at least 6 pairs of mice. (FIG. 1B) Knockdown of TR4 in macrophage RAW264.7 cells (RAW-TR4siRNA) reduces foam cell formation. RAW264.7 cells were infected with retrovirus expressing TR4-siRNA or control TR4-scramble. After selection with puromycin (5 g/ml) for 3 days, the cells were harvested and TR4 expression levels were examined by Western blot analysis (left panel). Right panel, RAW-TR4siRNA cells and their empty vector control cells were treated with 100 g/ml oxLDL for 24 hours. Oil red staining was performed. (FIG. 1C) Overxpression of TR4 in macrophage RAW264.7 cells (RAW-TR4) induces foam cell formation. RAW264.7 cells were stably transfected with pCDNA3-flag-TR4 or empty vector pCDNA3-flag. After selection with G418 (500 g/ml) for 2 weeks, the stable cells were harvested and TR4 protein expression were examined by Western blot analysis. GAPDH served as the loading control (left panel). Right panel, RAWTR4 cells and their empty vector control cells were treated with 8 g/ml oxLDL for 24 h. Oil red staining was performed.

(FIG. 2A) CD36 expression is reduced in $TR4^{-/-}$ mice. Peritoneal macrophages were isolated from $TR4^{+/+}$ and $TR4^{-/-}$ mice, respectively. CD36 mRNA (upper panel) and protein level (lower panel) were then examined by semi-quantitative RT-PCR, real-time PCR, and Western blot analysis. Data shown from two pairs of mice representing results from at least 6 pairs of mice with similar results. **, p<0.01. (FIG. 2B) Overexpression of TR4 enhances CD36 expression in mouse macrophage RAW264.7 cells. The stable cells RAW-TR4 and its control RAW-flag, which were established in FIG. 1C were harvested and CD36 mRNA levels were examined by real-time RT-PCR (left panel). The internal control was 18s rRNA and the CD36 mRNA expression in control (RAW-flag) cells was set as 1. The data represent mean±SD of triplicate samples. Right panel, the stable cells were harvested and CD36 and TR4 protein expression were examined by Western blot analysis. GAPDH served as the loading control. (FIG. 2C) Knockdown of TR4 expression reduces CD36 expression in mouse macrophage RAW264.7 cells. The RAW-TR4siRNA and RAWTR4scramble cells, which were established in FIG. 1B, were harvested and real-time RT-PCR was applied to examine the mRNA levels of TR4 (left panel) and CD36 (middle panel). The internal control was 18s rRNA and the mRNA expression in control (RAW-TR4scramble) cells was set as 1. The data represent mean±SD of triplicate samples. (FIG. 2D) Knockdown of TR4 expression reduces CD36 mRNA expression in primary-cultured mice peritoneal macrophage. Wild-type male mouse were injected intraperitoneally with 1 ml of 3.8% thioglycollate medium. After 4 days, mouse peritoneal macrophages were isolated and seeded on the plates and purified by 2 h adherence. The adherent macrophages were transduced with lentiviral vector package of TR4 specific siRNA (TR4-siRNA) or control scramble (TR4scramble) for 1 day, then the cells were harvested and real-time RT-PCR were applied to examine the mRNA levels of TR4 (left panel) and CD36 (right panel). The internal control was 18s rRNA and the mRNA expression in control (TR4scramble) cells was set as 1. The data represent mean±SD of triplicate samples.

(FIG. 3A) RAW-TR4siRNA cells were stably transfected with pCDNA3-flag-CD36 or empty vector. After selection with G418 (500 g/ml) for 2 weeks, the cells were harvested and the CD36 protein expressions were confirmed by Western blot analysis. (FIG. 3B) Overexpression of CD36 rescues TR4-mediated reduced foam cell formation. The cells, as indicated, were seeded on 96-well plates and exposed to 100 g/ml oxLDL for 24 h. Oil red staining was then performed. These data represent results from at least two independent experiments.

(FIG. 4A) TR4 dose-dependently enhanced CD36-luciferase activity. A schematic diagram of the CD36 promoter which contains TR4 DNA binding region (TR4RE) is illustrated. The CD36 promoter containing luciferase reporter construct (CD36-luc; 0.2 g) was co-transfected with increasing amount of pCMX-TR4 (0.2, 0.4 and 0.6 g) into CV-1 cells. The total amount of plasmids was adjusted to equality by the empty vector pCMX. The cells were harvested for the luciferase assay. The data with only CD36-luc transfection (lane 1) was set as 1 and results represent mean±SD. (FIG. 4B) TR4 can activate the activity of wild type CD36-luc, but not mutant (mt) CD36-luc. (FIG. 4C) TR4-siRNA reduces TR4-mediated CD36-luc activity. Reporter plasmids CD36-luc with TR4-siRNA or TR4scramble were transfected into H1299 cells as indicated. Then, the cells were harvested for luciferase assay. The data of lane 1 was set as 1 and results represent mean±SD.

(FIG. 5A) TR4 directly binds to the TR4RE site of the CD36 promoter region through EMSA supershift assay. The $^{32}$P-labeled probe was incubated with (lane 3-6) or without (lane 1-2) in vitro translated TR4 protein. Complexes were resolved on 4.5% polyacrylamide gels. The specific complexes are indicated by arrows. TR4 protein-DNA complexes were also incubated with TR4 antibody (lane 4). (FIG. 5B) TR4 directly binds to the promoter of CD36 through ChIP assay. RAW cells were cross-linked with formaldehyde (final 1%) for 15 min at room temperature, and then subjected to chromatin immunoprecipitation using an anti-TR4 antibody or IgG (negative control) and the indicated primers. Reaction products were resolved by electrophoresis. The results are representative of at least two independent experiments.

(FIG. 6A) PUFAs metabolites induced PPAR- and TR4-mediated CD36 activity. Increasing amounts of arachidonic acid (AA), ecosapentaenoic acid (EPA) (1, 10, 50, 100 and 250 M in BSA), and 15-HETE, 13-HODE (1 and 20 M in DMSO) were added 24 h after co-transfection of 0.6 g PPARγ/RXR or TR4 with 0.2 g CD36-luc into CV-1 cells. After 24 h, cells were harvested for Luciferase activity. The relative luciferase activity was calculated while setting pCMX-TR4 in vehicle control as 1. (FIG. 6B) Protease protective peptide mapping were analyzed in liganded-PPARγ and TR4. 15-HETE, 13-HODE, AA, and EPA were incubated with [$^{35}$S]-PPARγ, and [$^{35}$S]-TR4 for 15 min, then different concentrations of trypsin (0.25 and 2.5 g/ml) were added for another 10 min. The reaction was stopped by adding 2×SDS-sample buffer. The protease digestion pattern was resolved by gel electrophoresis in 12.5% (for PPARγ), and 16% (for TR4) SDS-PAGE. (FIG. 6C) Rosiglitazone dose-dependently activates PPARγ- and TR4-mediated CD36-luc activity. Rosiglitazone (0.1, 0.5, 1 and 3 M in DMSO) were added 24 h after co-transfection of 0.6 g PPARγ/RXR or TR4 with 0.2 g CD36-luc into CV-1 cells. After 24 h, cells were harvested for Luciferase activity. The relative luciferase activity was calculated while setting pCMX-TR4 in vehicle control as 1.

DETAILED DESCRIPTION

Figure 1A:
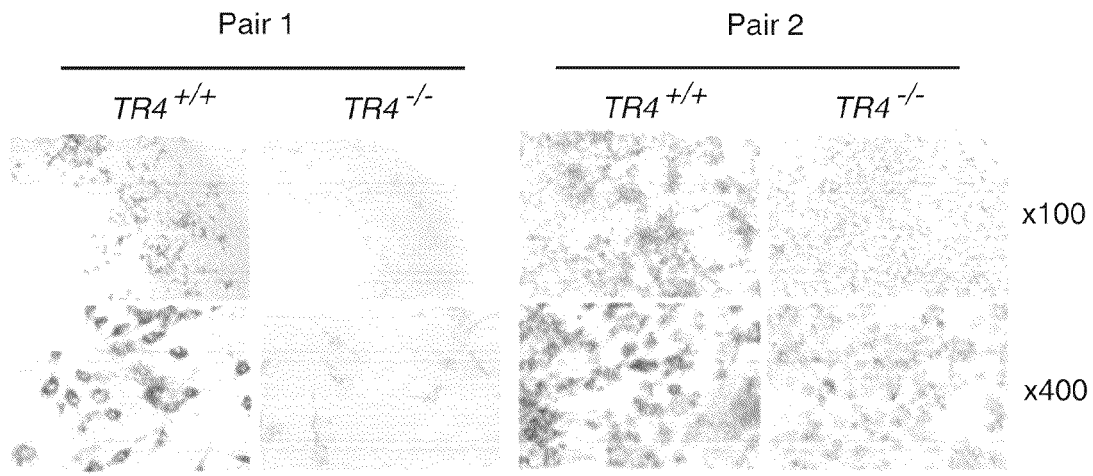
FIGS. 1A, 1B and 1C show that TR4 modulates foam cell formation.

The present compositions and methods may be understood more readily by reference to the following detailed description of preferred embodiments disclosed herein and the Examples included therein and to the Figures and their previous and following description.

Before the present compounds, compositions, articles, devices, and/or methods are disclosed and described, it is to be understood these are not limited to specific synthetic methods, specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

1. Abbreviations which May be Used

CAT, chloramphenicol acetyltransferase; DBD, DNA-binding domain; E2, 17β-estradiol; ER, estrogen receptor; ERE, estrogen response element; GST, glutathione S-transferase; LBD, ligand-binding domain; PR, progesterone receptor; TR2, Testicular orphan receptor 2, TR4, Testicular orphan receptor 4; RA, retinoic acid; PPARα, peroxisome proliferator-activated receptor α; CAT, chloramphenicol acetyltransferase; RAR, retinoic acid receptor; PPRE, peroxisome proliferator response element; 1,25-(OH)$_2$D$_3$, 1,25-dihydroxyvitamin D$_3$; Kd, equilibrium dissociation constant, TR4 associated constant; AR, androgen receptor; GR, glucocorticoid receptor; TR, thyroid hormone receptor; TR4RE, TR4 response element; TR4-N, TR4-N terminus; TR4-DL, TR4 DNA binding domain (DBD) and ligand binding domain (LBD); DR, direct repeat; HDACs, histone deacetylases; TSA, Trichostatin; EMSA, electrophoretic mobility shift assay; LUC, luciferase; −UL, minus uronolactone.

2. Activate

Activate and any form of same refers to increasing activity downstream from an event, and can be determined relative to a control.

3. Set

A set and any form of same refers to a collection of components. Such as a set of ligands, or a set of molecules, or a set of fatty acids. The members of a set must include at least two unique components, such as two unique molecules, and typically will include more than 2 unique components, but as long as there are at least 2 unique components, there may be multiple copies of the same component. For example, a set may have components, such as ligands A, B, and C, where there are 1 copy of A, 5 copies of B, and 2 copies of C. Thus this set of components, in this case ligands, consists of 3 unique members (ligands) and 8 total members (ligands).

4. Activation Inhibitor

An activation inhibitor and any form of same refers to a molecule that can inhibit the activation of a component.

5. TR4 Activation Inhibitor

A TR4 activation inhibitor and any form of same is an activation inhibitor that inhibits TR4 activation.

6. PPAR Activation Inhibitor

A PPAR activation inhibitor and any form of same is an activation inhibitor that inhibits PPAR activation.

7. Competitive Ligand Modulating PPAR Complexes

A competitive ligand modulating PPAR complex and any form of same is a class of ligand modulating PPAR complexes where the molecule competes with the ligand, an omega 3 fatty acid, for binding at the PPAR ligand binding site to modulate the PPAR activity.

8. Competitive Ligand Modulating TR4 Complexes

A competitive ligand modulating TR4 complex and any form of same is a class of ligand modulating TR4 complexes where the molecule competes with the ligand, an omega 3 fatty acid, for binding at the TR4 ligand binding site to modulate the TR4 activity.

9. Competitive PPAR Binding Molecule

A competitive PPAR binding molecule and any form of same is a PPAR binding molecule that competes with a PPAR ligand for binding.

10. Competitive TR4 Binding Molecule

A competitive TR4 binding molecule and any form of same is a TR4 binding molecule that competes with a TR4 ligand for binding.

11. Components

A component and any form of same is a constituent part; element; ingredient. For example, a component can be a molecule, a compound, a composition, or a material, as well as classes of these.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular TR4 ligand is disclosed and discussed and a number of modifications that can be made to a number of molecules including the TR4 ligand are discussed, specifically contemplated is each and every combination and permutation of TR4 ligand the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

12. Control

The terms "control" or "control levels" or "control cells" and any forms of same are defined as the standard by which a change is measured, for example, the controls are not subjected to the experiment, but are instead subjected to a defined set of parameters, or the controls are based on pre- or post-treatment or experiment levels. They can either be run in parallel with or before or after a test run, or they can be a pre-determined standard. Or they are subjected to the experiment in a defined way and are a standard the non-control is compared to.

13. Decrease

A "decrease" and any form of same can refer to any change that results in a smaller amount of for example, an activity, such as TR4 binding activity. Thus, a "decrease" can refer to a reduction in an activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. Thus, for example, a decrease in the amount of activity can include but is not limited to a 10%, 20%, 30%, 40%, 50%, 60%, 70%, 80%, 90%, or 100% decrease.

14. Elution Molecule

An elution molecule and any form of same is any molecule that is capable of competing with an interaction between two molecules and which is in elution wash. In certain circumstances it is an elution molecule when in the wash and when a competitive binding reaction for a particular molecule.

15. Elution Wash

An elution wash and any form of same is a wash that is designed to "elute" a non-covalently bound molecule bound to another molecule, such as a molecule bound to a support. Typically elution washes are designed to disrupt interactions where as a typical "wash" is designed not to disrupt interactions an elution wash is designed to disrupt non-covalent interactions, either through, for example, denaturation or for example competitive binding. An elution wash can contain an elution molecule.

16. Expression Construct

An expression construct and any form of same is a DNA molecule having a transcribable cassette within in. The transcribable cassette can also be translatable after transcription. The transcribable cassette can include for example, a DNA sequence encoding for a protein, such as a protein or polypeptide encoding sequence, such as a gene. The transcribable cassette can also include, for example, an antisense, ribozyme, aptamer, shRNA or siRNA.

17. Fatty Acids

Fatty acids and any form of same can be saturated, unsaturated, or a mixture of saturated and unsaturated fatty acids. By "saturated" is meant that the molecule contains no carbon-carbon double or triple bounds. By "unsaturated" is meant that the molecule contains at least one carbon-carbon double or triple bond. In one aspect, the loading substance can be an omega-3 fatty acid. Examples of omega-3 fatty acids include, but are not limited to, α-linolenic acid (18:3ω3), octadecatetraenoic acid (18:4ω3), eicosapentaenoic acid (20:5ω3) (EPA), docosahexaenoic acid (22:6ω3) (DHA), docosapentaenoic acid (22:5ω3) (DPA), eicosatetraenoic acid (20:4ω3), uncosapentaenoic acid (21:5ω3), docosapentaenoic acid (22:5ω3) and derivatives thereof and mixtures thereof. Many types of derivatives of omega-3 fatty acids are well known in the art. Examples of suitable derivatives include, but are not limited to, esters, such as phytosterol esters, branched or unbranched $C_1$-$C_{30}$ alkyl esters, branched or unbranched $C_2$-$C_{30}$ alkenyl esters, or branched or unbranched $C_3$-$C_{30}$ cycloalkyl esters such as phytosterol esters and $C_1$-$C_6$ alkyl esters. Sources of oils can be derived from aquatic organisms (e.g., anchovies, capelin, Atlantic cod, Atlantic herring, Atlantic mackerel, Atlantic menhaden, salmonids, sardines, shark, tuna, etc) and plants (e.g., flax, vegetables, etc) and microorganisms (e.g., fungi and algae).

The term "omega-3", "n-3", "ω-3", "omega n-3", and "n-3 series" and any forms of same refers to a family of polyunsaturated fatty acids which have in common a carbon-carbon double bond in the ω-3 position. For example, the term "omega-3" signifies that the first double bond exists as the third carbon-carbon bond from the terminal methyl end (w) of the carbon chain.

The term "omega-6", "n-6", "ω-6", "omega n-6", and "n-6 series" and any forms of same refers to a family of polyunsaturated fatty acids which have in common a carbon-carbon double bond in the ω-6 position. For example, omega-6 signifies that the first double bond exists as the sixth carbon-carbon bond from the terminal methyl end (ω) of the carbon chain.

The term "omega-9", "n-9", "ω-9", "omega n-9", and "n-9 series" and any forms of same refers to a family of polyunsaturated fatty acids which have in common a carbon-carbon double bond in the ω-9 position. For example, omega-9 signifies that the first double bond exists as the ninth carbon-carbon bond from the terminal methyl end (w) of the carbon chain. All double bonds are in the cis-configuration, i.e. the two hydrogen atoms are on the same side of the double bond.

Fatty acids are hydrocarbon chains that terminate in a carboxyl group, being termed unsaturated if they contain at least one carbon-carbon double bond, and polyunsaturated when they contain multiple such bonds. Long-chain polyunsaturated fatty acids (PUFA) or highly-unsaturated fatty acids (HUFA), may be divided into the (n-3) and (n-6) series as a result of the location of these double bonds. PUFAs may include linoleic acid, docosahexaenoic acid or eicosapentainoic acid and PUFA metabolites may include comprises 15-HETE or 13-HODE.

There is overwhelming scientific evidence that (n-3) highly unsaturated fatty acids such as DHA have a positive effect on cardio-circulatory diseases, chronic inflammation and brain disorders. The (n-6) fatty acids on the other hand have been noted as intermediate metabolites within the eicosanoid steroids, such as prostaglandins, leukotrienes or the like.

Polyunsaturated fatty acids can comprise 1, 2, 3, 4, 5, 6, 7, 8, 9, or 10 double and/or triple carbon-carbon bonds. For example, polyunsaturated fatty acids can comprise 3-8, 4-7, or 5-6 double and/or triple carbon-carbon bonds. Currently, the main source of these highly unsaturated fatty acids is fish, with EPA and DHA noted within various fish species (such as sardines, anchovies, pilchards and tuna) at amounts around 20% and 10%, respectively. Yet, if one intends to use fish oil as the sole source of these lipids, several disadvantages exist, such as problems with flavor taint, uncontrollable fluctuations in availability, natural fish oil content variability, as well as the potential to accumulate harmful environmental pollutants if not processed correctly. In addition, if one intends to obtain a highly purified (n-3) or (n-6) oil from said sources, it is very difficult to preferentially separate and purify the desired oils without extensive processing. Fatty acids can also be isolated from Algal sources. Various microorganisms (mainly marine) are able to produce and/or accumulate the (n-3) series of docosahexaenoic acid. Of particular interest is the fact that microbial production is not subject to fluctuations caused by external variables such as seasonality, weather and food supply. For example, the following oil producing microbes are known as having the ability to produce DHA: the deep-sea derived bacterium *Vibrio marinus* (ATCC 15381), *Vibrio* sp. T3615.

18. Increase

An "increase" and any form of same can refer to any change that results in a larger amount of a activity, such as TR4 activity. Thus, for example, an increase in the amount in TR4 activity can include but is not limited to a 10%, 20%, 30%, 40%, 50%, 60%, 70%, 80%, 90%, or 100% increase.

19. Inhibit

"Inhibit," "inhibiting," and "inhibition" and any forms of same mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

20. Interact or Contact

Interact or contact and any forms of same means that two (or more) molecules touch one another in a way beyond the touching that takes place because of random touches between molecules. "Interacts" or "contacts" can be thought of as "binding" between two or more molecules, and therefore can have dissociation and association constants as well as equilibrium constants. For example, where appropriate, such as between a ligand or molecule competing with a ligand and its cognate binding partner, such as a protein, such as TR4 or PPAR, can have dissociation constants of less than or equal to $10^{-3}$, $10^{-4}$, $10^{-5}$, $10^{-6}$, $10^{-7}$, $10^{-8}$, $10^{-9}$, $10^{-10}$, $10^{-11}$, or $10^{-12}$.

21. Isolating

"Isolating" and any form of same such as "isolate" refer to a situation where something is in a form wherein it can be manipulated or further purified. Isolated and its forms indicates that something is in a current state which is different than a previous state. For example, a ribosomal RNA molecule can be "isolated" if it is, for example removed from an organism, synthesized or recombinantly produced. Often, the "isolation" of one thing is in relation to something else. It is understood that unless specifically indicated otherwise, any of the disclosed compositions can be isolated as disclosed herein.

22. Ligand Modulating PPAR Complex

A ligand modulating PPAR complex and any form of same is class of PPAR complex where the molecule interacting with PPAR interacts such that an effect on PPAR activity is modulated through the ligand domain of PPAR.

23. Ligand Modulating TR4 Complex

A ligand modulating TR4 complex and any form of same class of TR4 complex where the molecule interacting with TR4 interacts such that an effect on TR4 activity is modulated through the ligand domain of TR4.

24. Linked TR4

A linked TR4 and any form of same is a TR4 which has been attached to a support. This can be done, for example, using capture tags as discussed herein.

25. Linked PPAR

A linked PPAR and any form of same is a PPAR which has been attached to a support. This can be done, for example, using capture tags as discussed herein.

26. Modulate

To modulate and any form of same means either increasing, decreasing, or maintaining an activity. It is understood that wherever one of these words is used it is also disclosed that it could be at least 1%, 5%, 10%, 20%, 50%, 100%, 500%, or 1000% increased from a control, or it could be at least 1%, 5%, 10%, 20%, 50%, or 100% decreased from a control.

27. Molecule

A molecule and any form of same is any chemical, biochemical, or biological entity that is uniquely defined, by for example, having an individual molecular weight and properties. For example, a molecule can be an organic molecule, such as methanol. It could be a protein, or a gene. A molecule can be a compound or composition as long it has have individual unique properties. Unless specifically indicated, the word "molecule" would include the specific molecule and salts thereof, such as pharmaceutically acceptable salts. Other classes of molecules include known and unknown molecules. A known molecule is a designation in which a particular property is known, such as structure or activity. Known is typically used in the context of a control or in a comparison. An unknown molecule is not a known molecule.

28. Non-Binding Molecules

A non binding molecule and any form of same is a molecule which does not interact as defined herein with a particular binding partner, such as PPAR or TR4.

29. Non-Competitive Modulating PPAR Complexes

A non-competitive modulating PPAR complex and any form of same is a class of ligand modulating PPAR complexes where the molecule does not compete with the ligand, an omega 3 fatty acid, for binding at the PPAR ligand binding site but still has an effect on modulate the PPAR activity through the ligand binding site, i.e. an effect on ligand induced activity of PPAR.

30. Non-Competitive Modulating TR4 Complexes

A non-competitive modulating TR4 complex and any form of same is a class of ligand modulating TR4 complexes where the molecule does not compete with the ligand, an omega 3 fatty acid, for binding at the TR4 ligand binding site but still has an effect on modulate the TR4 activity through the ligand binding site, i.e. an effect on ligand induced activity of TR4.

31. Non-Competitive PPAR Binding Molecule

A non-competitive PPAR binding molecule and any form of same is a PPAR binding molecule that binds PPAR non-competitively with a PPAR ligand, but which modulates the activity of the ligand with PPAR.

32. Non-Competitive TR4 Binding Molecule

A non-competitive TR4 binding molecule and any form of same is a TR4 binding molecule that binds TR4 non-competitively with a TR4 ligand, but which modulates the activity of the ligand with TR4.

33. Obtaining a Tissue Sample

"Obtaining a tissue sample" or "obtain a tissue sample" and any forms of same means to collect a sample of tissue from a subject or measure a tissue in a subject. It is understood and herein contemplated that tissue samples can be obtained by any means known in the art including invasive and non-invasive techniques. It is also understood that methods of measurement can be direct or indirect. Examples of methods of obtaining or measuring a tissue sample can include but are not limited to tissue biopsy, tissue lavage, aspiration, tissue swab, spinal tap, magnetic resonance imaging (MRI), Computed Tomography (CT) scan, Positron Emission Tomography (PET) scan, and X-ray (with and without contrast media).

34. Optional

"Optional" or "optionally" and any form of same means that the subsequently described event or circumstance may or may not occur, and that the description includes instances where said event or circumstance occurs and instances where it does not.

35. PPAR Binding Molecule

A PPAR binding molecule and any form of same is any molecule which can interact with PPAR and can form a PPAR complex. PPAR binding molecules include competitive and non-competitive PPAR binding molecules.

36. PPAR Complex

A PPAR complex and any form of same is a composition composed of PPAR and another molecule which has interacted with the PPAR as defined herein. A unique class of PPAR complexes are those that involve molecules which have an effect modulated through the ligand binding site. These are called ligand modulating PPAR complexes. One subclass of ligand modulating PPAR complexes is the competitive ligand modulating PPAR complexes. Another class is a non-competitive modulating PPAR complexes.

37. PPAR Expression Construct

A PPAR expression construct and any form of same is an expression construct where the transcribable cassette encodes for a PPAR protein or fragment, such as a functional fragment.

38. PPAR Non-Binding Molecules

A PPAR non-binding molecule and any form of same is a non-binding molecule where the particular partner is PPAR.

39. PPAR Response Element-Reporter Expression Construct

A PPAR response element reporter expression construct and any form of same is an expression construct where a PPAR response element has been attached to an reporter expression construct, such that expression of the reporter indicates activation by PPAR binding its response element. This can also be used in the negative, i.e. loss of activity.

40. Primers

"Primers" and any form of same are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

41. Probes

"Probes" and any form of same are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

42. Purify

"Purify" and any form of same such as "purifying" refers to the state in which a substance or compound or composition is in a state of greater homogeneity than it was before. It is understood that as disclosed herein, something can be, unless otherwise indicated, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% pure. For example, if a given composition A was at least 90% pure, this would mean that at least 90% of the composition was A, and that 10% or less of the composition was one or more things, such as molecules, compounds, or other substances. Unless otherwise indicated, purity will be determined by the relative "weights" of the components within the composition. It is understood that unless specifically indicated otherwise, any of the disclosed compositions can be purified as disclosed herein.

43. Ranges

Ranges and any form of same can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between "10" and "15." It is also understood that each unit between two particular units are also disclosed. For example, if "10" and "15" are disclosed, then "11," "12," "13," and "14" are also disclosed.

44. Reporter Expression Construct

A reporter expression construct and any form of same is an expression construct where the transcribable cassette encodes for "reporter gene" where a reporter gene is any transcribable cassette which when expressed alternatively as RNA or polypeptide or protein, or both can be tracked as an indication of an activity, such as transcription from a particular response element or of binding by a ligand on a steroid receptor which causes the steroid receptor to activate a gene. Examples of a reporter gene as discussed herein are "markers." Examples of a marker or a reporter would be luciferase or β-galactosidase.

45. Support

Support and any form of same refers to a material beyond a particular molecule which is meant to provide structure or a matrice. For example, agarose or sepharose is a "support" which can be attached to a molecule. As used herein, typically a support can be or is linked to a molecule, such as TR4 or PPAR or an omega-3 fatty acid.

46. System

A system and any form of same refers to a collection of components which have a certain function or activity. For example, a cell that is transfected with a particular nucleic acid that is expressed can be a system that can be used for the expression of the cognate nucleic acid.

47. TR4 Binding Molecule

A TR4 binding molecule and any form of same is any molecule which can interact with TR4 and can form a TR4 complex. TR4 binding molecules include competitive and non-competitive TR4 binding molecules.

48. TR4 Complex

A TR4 complex and any form of same is a composition composed of TR4 and another molecule which has interacted with the TR4 as defined herein. A unique class of TR4 complexes are those that involve molecules which have an effect modulated through the ligand binding site. These are called ligand modulating TR4 complexes. One subclass of ligand modulating TR4 complexes is the competitive ligand modulating TR4 complexes. Another class is a non-competitive modulating TR4 complexes.

49. TR4 Expression Construct

A TR4 expression construct and any form of same is an expression construct where the transcribable cassette encodes for a TR4 protein or fragment, such as a functional fragment.

50. TR4 Non-Binding Molecules

A TR4 non-binding molecule and any form of same is a non-binding molecule where the particular partner is TR4.

51. TR4 Response Element-Reporter Expression Construct

A TR4 response element reporter expression construct and any form of same is an expression construct where a TR4 response element has been attached to an reporter expression construct, such that expression of the reporter indicates activation by TR4 binding its response element. This can also be used in the negative, i.e. loss of activity.

52. Transcription Activity

Transcription activity and any form of same as used herein refers to the activity of a particular protein has as an activator of transcription. There are many ways that this activity can be determined, for example, CAT assays or luceriferase assays are two examples used herein.

53. Treatment

"Treatment," "treat," or "treating" and any forms of same mean a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression. For example, a disclosed method for reducing the effects of prostate cancer is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition.

54. Wash

A "wash" and any form of same refers to its common usage, where a typically inert or limited reactive fluid, such as a buffer, is applied to a mixture, such as a solid support with a molecules attached and other molecules which may be non-covalently bound. It is understood that as disclosed herein, the methods can have a wash step applied after every other step recited in any method, and in fact a wash step is optionally specifically disclosed for all such steps. A general wash, such as a non-elution wash, is designed to be non disruptive to non-covalent interactions which may be taking place between two molecules. While nothing is a 100%, a wash only disrupt less than 1%, 2%, 3%, 4%, 5%, 6%, 7%, 8%, 9%, 10%, 15%, or 20% of interactions as determined by the amount of a particular molecule in the collected wash.

B. COMPOSITIONS AND METHODS

Disclosed herein, TR4 knockout (TR4) mice were used to study its function in cardiovascular diseases, and it was shown that CD36 expression was reduced with reduced foam cell formation in TR4−/− mice. Mechanistic dissection indicated that TR4 induced CD36 protein and mRNA expression via transcriptional regulation. It was found that this TR4-mediated CD36 transactivation can be further enhanced by polyunsaturated fatty acids (PUFAs), such as Omega-3 and -6 fatty acids, and their metabolites and thiazolidinedione (TZD)-rosiglitazone. Both EMSA and ChIP assays demonstrated that TR4 binds to the TR4 response element located on the CD36 5'-promoter region for the induction of CD36 expression. Stably transfected TR4-siRNA or functional TR4 cDNA in the RAW264.7 macrophage cells resulted in either decreased or increased CD36 expression with decreased or increased foam cell formation, respectively. Restoring functional CD36 cDNA in the TR4 knockdown macrophage cells reversed the decreased foam cell formation. Together, these results reveal a signaling pathway controlling CD36-mediated foam cell formation/cardiovascular diseases, and indicate that TR4 transactivation can be activated via its ligands/activators, such as PUFA metabolites and TZD. These results provided a platform to screen composition(s) for modulating PPAR and TR4 as well as metabolism syndrome, diabetes and cardiovascular diseases.

a) Atherosclerosis

Atherosclerosis is a disease of both lipid disorder and chronic inflammation that results from interactions of modified lipoproteins, monocyte-derived macrophages, T cells, and cells from the vessel wall (Glass et al. Cell, 2001). Uptake of lipids transforms macrophages into arterial foam cells, a critical step in atherogenesis. This uptake is mediated by specific macrophage scavenger receptors, including CD36 (Endemann et al. J Biol Chem, 1993) and scavenger receptor A (SRA) (Kodama et al. PNAS, 1988), that recognize and internalize modified lipoproteins such as the oxidized forms of low-density lipoproteins (oxLDL). Combined inhibition of SRA and CD36 blocks human and murine foam cell formation in vitro, and CD36 accounts for a large proportion of oxLDL uptake by macrophages (Febbraio et al. J Bil Chem, 1999; Kunjathoor et al. J biol Chem, 2002; Suzuki et al. Nature, 1997; Febbraio et al. J Clin Invest, 2000). Furthermore, oxLDL induces CD36 dependent c-jun N-terminal kinase activity, which is needed for oxLDL-mediated foam cell formation (Rahaman et al. Cell Metab, 2006). Although the role of CD36 in oxLDL-mediated foam cell formation in vitro is clear, the in vivo roles of CD36 on atherosclerosis, assessed by atherogenic mouse models, are equivocal, with reports for CD36 as either atherogenic (Suzuki et al. Nature, 1997; Febbraio et al. J Clin Invest, 2000; Babaev et al. Arterioscler Thromb Vasc Biol) or atheroprotective (Witztum J Clin Invest, 2005; van Berkel et al. Curr Opin Lipidol, 2005; Moore et al. J Clin Invest, 2005). CD36 can be up-regulated by different molecules that are directly or indirectly mediated through PPARs. For instance, up-regulation of CD36 by oxidized LDL and linoleic acid involves activation of PPAR (Kliewer et al. Science, 1999; Nagy et al. Cell, 1998). Other PPAR ligands, such as 15d-PGJ2 and the TZD class of antidiabetic drugs also induce CD36 expression (Kliewer et al. Cell, 1995, Forman et al. Cell, 1995; Tontonoz et al. Curr Opin Genet Dev, 1995; Lehmann et al. J Biol Chem, 1995). The CD36 promoter contains PPAR/RXR binding site, and PPAR/RXR can modulate CD36 gene expression through direct promoter interaction (Tontonoz et al. Cell, 1998).

Testicular orphan nuclear receptor 4 (TR4) belongs to the nuclear receptor superfamily with no ligands being identified thus far. TR4 is closely related to TR2, RXRs, and hepatocyte nuclear factor 4 (Lee et al. J Steroid Biochem Mol Biol, 2002). The expression of TR4 was found at moderate to high levels in all tissues tested (Yang et al. Cell, 2006; Bookout et al. Cell, 2006). TR4 null (TR4$^{-/-}$) mice have significant growth retardation (Collins et al. PNAS, 2004), defects in female reproductive function and maternal behavior (Collins et al. PNAS, 2004), impaired cerebella function (Chen et al. Mol Cell Biol, 2005), reduced sperm production (Mu et al. Mol Cell Biol, 2004), and reduced myelination (Zhang et al. Mol Endocrinol, 2007). TR4 can be a master regulator, controlling glucose and lipid metabolism (Liu et al. Diabetes, 2007), which is consistent with a previous report that TR4 has a strong circadian expression in key metabolic tissues, including fat, liver, and muscle (Yang et al. Cell, 2006; Bookout et al. Cell, 2006). TR4 is also highly expressed in immune cells and macrophages. However, its roles within the macrophage remain unknown (Schote et al. Mol Immunol, 2007; Barish et al. Mol Endocrinol, 2005).

Herein, a signaling pathway was identified that regulates CD36 and foam cell formation by TR4 both in vitro and in vivo. This TR4-mediated CD36 induction can be activated by its endogenous and exogenous ligands/activators. These findings indicate that TR4 is a new member of the nuclear receptor superfamily that plays important roles in metabolism syndrome, diabetes and cardiovascular diseases.

2. TR4 Receptor

The TR4 receptor is a member of the nuclear receptor superfamily. The nuclear receptor superfamily is comprised of transcription factors that are related by sequence and structure, yet are specifically induced or repressed by a wide variety of chemical compounds. Functioning as transcription factors, nuclear receptors can control the expression of target genes and thereby direct developmental, physiological, and behavioral responses from the cellular level to that of the whole organism (Beato, M. Faseb J, 5: 2044-2051, 1991; Beato, M. and Klug, J. Hum Reprod Update, 6: 225-236, 2000). The structural features common to nuclear receptors include those required for ligand binding, dimerization, DNA binding, and transactivation. Binding of a particular receptor to a specific DNA sequence or hormone response element (HRE) within the promoter of one of its target genes is mediated by a DNA binding domain that contains two zinc finger motifs.

Both embryonic and adult tissue distribution analysis demonstrated that TR4 is expressed mainly in neural and testis during embryonic development. In situ hybridization experiments using TR4 specific probes have shown transcripts present in actively proliferating cell populations of the brain and peripheral organs during embryonic development. The expression of TR4 at sites of sensory innervation and in sensory organs throughout embryogenesis indicate an important role for these receptors in this critical aspect of nervous system development. Additionally, high expression of TR4 in the developing brain and spinal cord, including specific expression in motor neurons, show that these receptors can be involved in the proper development of movement and limb coordination (Young et al. J Biol Chem, 272: 3109-3116, 1997).

TR4 is closely related to the retinoic X receptor (RXR), and binds to AGGTCA DNA sequence motifs in direct repeat orientation, with variable spacing, in the promoters of its target genes (Chang et al. Proc Natl Acad Sci USA, 91: 6040-6044, 1994). Therefore, TR4 can directly influence gene activation by directly binding to DNA and activating genes such as ApoE and Vitamin D receptor (VDRE) (Kim et al. J Biol Chem, 278: 46919-46926, 2003; Lee et al. J Biol Chem, 274: 16198-16205, 1999). On the other hand, TR4 acts as a suppressor to influence other receptor functions, such as RXR/retinoic acid receptor (RAR), androgen receptor (AR), and estrogen receptor (ER) (Lee et al. J Biol Chem, 273: 13437-13443, 1998; Lee et al Proc Natl Acad Sci USA, 96: 14724-14729, 1999; Shyr et al. J Biol Chem, 277: 14622-14628, 2002) by competition for the same DNA binding sites or through protein-protein interactions.

In vitro data show that TR4 functions as a master regulator to modulate many signaling pathways. To investigate TR4 function, mice lacking TR4 (TR4 KO) via targeted gene disruption have been created (Collins et al. Proc Natl Acad Sci USA, 101:15058-15063, 2004, herein incorporated by reference in its entirety for its teaching concerning TR4 KO mice).

Also disclosed are methods of treating a subject with cardiovascular disease or for example, diabetes, comprising administering to the subject an agent that modulates TR4 activity or PPAR activity as discussed herein, wherein an decrease in TR4 activity decreases cardiovascular disease and wherein preferred PPAR binding molecules are those that interact with PPAR but not TR4.

Disclosed are methods for testing a compound for an effect on a disease discussed herein, such as cardiovascular disease or diabetes or other TR4 or PPAR related diseases or disorders comprising administering the compound to an animal and assaying for TR4 activity or PPAR activity or both, wherein an increase in TR4 activity indicates a compound that may increase cardiovascular disease risk, and a compound that increases PPAR activity may be a compound that decreases diabetes, and where compounds that increase PPAR activity without increasing TR4 activity can be molecules useful for diabetes or other pPAR related disorders. It is understood that testing, screening, or evaluation of compositions (e.g., a compound or drug) for effects on diseases as discussed herein can utilize TR4 knockout animals. Therefore, also disclosed are methods of testing a composition for an effect on diseases discussed herein comprising administering the composition to a TR4 knockout animal, and performing an assay related to a disease discussed herein, wherein a change in the assay relative to a control indicates the composition has an effect on the disease discussed herein.

Disclosed are methods for evaluating whether a treatment with a compound should be performed due to the effect the treatment has on a disease discussed herein, wherein the compound modulates the TR4 activity, PPAR activity, or both, the method comprising a) exposing cells to the compound, and b) evaluating TR4 activity in the presence of the compound, wherein a change in the TR4 activity of the subject, relative to the TR4 activity of a subject that has not been exposed to the compound, indicates that the compound modulates TR4 activity, and wherein a decrease in TR4 activity indicates a negative effect on a disease as discussed herein, providing an indication that treatment with the compound may not be indicated. In addition, these steps can be performed for PPAR activity.

3. PPAR

Peroxisome proliferator-activated receptors or PPARs are a group of nuclear transcription factor isoforms that are closely connected to cellular metabolism and cell differentiation. To date, three types of PPARs have been identified. PPAR-α is expressed in certain tissues, including the liver, kidneys, heart, muscle and adipose. PPAR-γ, although transcribed by the same gene, exists in three forms. PPAR-γ 1 is expressed in virtually all tissues, including the heart, muscle, colon, kidneys, pancreas and the spleen. PPAR-γ 2 is expressed mainly in adipose tissue. PPAR-γ 3 is expressed in macrophages, the large intestine and white adipose tissue. PPAR-δ is expressed in a variety of tissues, including the brain, adipose and skin.

PPARs heterodimerize with retinoid X receptor (RXR) and bind to specific elements on the DNA of target genes called PPAR response elements. The binding of PPAR to its ligand then leads to an increase or decrease in gene expression. There are several known PPAR ligands such as, thiazolidinedione (TZD), fatty acids and the prostaglandin D2 metabolite 15d-PGJ2. The genes activated by PPAR-γ stimulate lipid uptake by fat cells.

There are three variants of PPARγ. Variants 1 and 3 have identical protein sequences. Variant 2 (protein id NP_056953) has the same protein sequence as variants 1 and 3 but has the addition of 28 amino acids on the N-terminal end MGETLGDSPIDPESDSFTDTLSANISQE (SEQ ID NO:5).

The majority of the nucleotide sequences are identical but there is variation at the N-terminal end of each variant. The first 169 bp of variant 1 are not present in variant 3. The first 196 bp of variant 3 are not present in variant 1. The final 1723 bp of variants 1 and 3 are identical.

The final 1648 bp of variants 1 and 2 are identical. The first 244 bp of variant 1 are not present in variant 2. The first 172 bp of variant 2 are not present in variant 4. Methods Disclosed are methods of screening molecules comprising: incubating a molecule with a TR4 forming a TR4 complex; collecting molecules that do not form a TR4 complex, wherein the molecules that do not form a TR4 complex are called TR4 non-binding molecules; incubating the TR4 non-binding molecules with PPAR; and collecting the molecules that form a PPAR complex, wherein the molecules that form a PPAR complex are called PPAR binding molecules.

Also disclosed are methods, wherein incubating the molecule with TR4, comprises combining a molecule and TR4 in a mixture allowing for contact between the molecule and TR4, wherein collecting molecules that do not form a TR4 complex comprises: a TR4 linked to a support, forming a linked TR4; and passing the molecules over the linked TR4, wherein the support linked to TR4 comprises sepharose, an agarose bead or an antibody, wherein the linked TR4 comprises a covalent bond between the support and TR4, wherein the linked TR4 comprises a non-covalent bond between the support and TR4, wherein collecting the molecules that form a PPAR complex comprises: PPAR linked to a support, forming a linked PPAR; passing the TR4 non-binding molecules over the linked PPAR; and eluting the molecules bound to the linked PPAR, wherein the support linked to TR4 comprises sepharose, agarose beads or antibodies, wherein the linked PPAR comprises a covalent bond between the support and PPAR, wherein the linked PPAR comprises a non-covalent bond between the support and PPAR, wherein eluting the molecules bound to linked PPAR comprises: washing the linked PPAR with a wash comprising an elution molecule; washing the linked PPAR with a wash comprising a low or high pH buffer; or washing the linked PPAR with a wash comprising a detergent, wherein the elution molecule is an PUFA, and/or wherein the PUFA comprises an omega-3 fatty acid.

Disclosed are methods of screening molecules comprising: incubating a molecule with a PPAR forming a PPAR complex; collecting molecules that do not form a PPAR complex wherein the molecules that do not form a PPAR complex are called PPAR non-binding molecules; incubating the PPAR non-binding molecules with TR4; and collecting the molecules that form a TR4 complex, wherein the molecules that form a TR4 complex are called TR4 binding molecules.

Also disclose are methods wherein incubating the molecule with PPAR, comprises combining a composition and PPAR in a mixture allowing for contact between the composition and PPAR, wherein collecting molecules that do not form a PPAR complex comprises: PPAR linked to a support, forming a linked PPAR; and passing the molecules over the linked PPAR, wherein the support linked to PPAR comprises sepharose, an agarose bead or an antibody, wherein the linked PPAR comprises a covalent bond between the support and PPAR, wherein the linked PPAR comprises a non-covalent bond between the support and PPAR, wherein collecting the molecules that form a TR4 complex comprises: TR4 linked to a support, forming a linked TR4; passing the PPAR non-binding molecules over the linked TR4; and eluting the molecules bound to the linked TR4, wherein the support linked to PPAR comprises sepharose, agarose beads or antibodies, wherein the linked TR4 comprises a covalent bond between the support and TR4, wherein the linked TR4 comprises a non-covalent bond between the support and TR4, wherein eluting the molecules bound to linked TR4 comprises: washing the linked TR4 with a wash comprising an elution molecule; washing the linked TR4 with a wash comprising a low or high pH buffer; or washing the linked TR4 with a wash comprising a detergent, and/or wherein the elution molecule comprises an omega-3 fatty acid.

Disclosed are methods of screening molecules comprising: incubating a molecule with a TR4 forming a TR4 complex; collecting molecules that form a TR4 complex, wherein the molecules that form a TR4 complex are called TR4 binding molecules; incubating the TR4 binding molecules with PPAR; and collecting the molecules that form a PPAR complex, wherein the molecules that form a PPAR complex are called PPAR binding molecules.

Also disclosed are methods wherein incubating a molecule with TR4, comprises combining a molecule and TR4 in a mixture allowing for contact between the molecule and TR4, wherein collecting the TR4 binding molecules comprises: TR4 linked to a support, forming a linked TR4; and passing the molecules over the linked TR4, and eluting the molecules bound to TR4, wherein the support linked to TR4 comprises sepharose, an agarose bead or an antibody, wherein the linked TR4 comprises a covalent bond between the support and TR4, wherein the linked TR4 comprises a non-covalent bond between the support and TR4, wherein eluting the molecules bound to linked TR4 comprises: washing the linked TR4 with a wash comprising an elution molecule; washing the linked TR4 with a wash comprising a low or high pH buffer; or washing the linked TR4 with a wash comprising a detergent, wherein collecting the PPAR binding molecules comprises: a PPAR linked to a support, forming a linked PPAR; passing the TR4 binding molecules over the linked PPAR; and eluting the molecules bound to linked PPAR, wherein the support linked to PPAR comprises sepharose, an agarose bead or an antibody, wherein the linked PPAR comprises a covalent bond between the support and PPAR, wherein the linked PPAR comprises a non-covalent bond between the support and PPAR, wherein eluting the molecules bound to linked PPAR comprises: washing the linked PPAR with a wash comprising an elution molecule; washing the linked PPAR with a wash comprising a low or high pH buffer; or washing the linked PPAR with a wash comprising a detergent, and/or wherein the competing molecule is an omega-3 fatty acid.

Disclosed are compositions comprising a cell wherein the cell comprises a TR4 expression construct, a TR4 response element-reporter expression construct, a PPAR expression construct and a PPAR response element-reporter expression construct.

Also disclosed are compositions wherein the TR4 response element-reporter expression construct comprises luciferase or β-galactosidase, wherein the PPAR response element-reporter expression construct comprises luciferase or β-galactosidase, wherein the PPAR response element-reporter expression construct comprises luciferase or β-galactosidase, and/or wherein the PPAR response element-reporter expression construct is different than the TR4 response element-reporter expression construct.

Disclosed are methods of making a cell comprising co-transfecting a cell with a TR4 expression construct, a TR4 response element-reporter expression construct, a PPAR expression construct and a PPAR response element-reporter expression construct.

Also disclosed are methods wherein the co-transfecting comprises a vector, wherein the vector comprises a viral vector.

Disclosed are methods of identifying a modulator comprising incubating a cell from claim 39 with a molecule; determining if the molecule activated the TR4 response-element reporter construct, and determining if the molecule activated the PPAR response-element reporter construct.

Disclosed are methods, further comprising the step of isolating the molecule if the molecule activated the TR4 response-element reporter construct, further comprising the step of isolating the molecule if the molecule did not activate the PPAR response-element reporter construct, further comprising the step of isolating the molecule if the molecule activated the PPAR response-element reporter construct, further comprising the step of isolating the molecule if the molecule did not activate the TR4 response-element reporter construct, further comprising the step of isolating the molecule if the molecule activated the TR4 response-element reporter construct, wherein step b) comprises comparing the amount of expression from the expression construct to a control, wherein step c) comprises comparing the amount of expression from the expression construct to a control, wherein step c) comprises comparing the amount of expression from the expression construct to a control, and/or wherein the molecule comprises a known molecule, an unknown molecule or a set of molecules.

Disclosed are compositions comprising an isolated TR4 complex and a PUFA or PUFA metabolite.

Also disclosed are compositions wherein the PUFA comprises linoleic acid, docosahexaenoic acid or eicosapentainoic acid, and/or wherein the PUFA metabolite comprises 15-HETE or 13-HODE.

Disclosed are methods of treating or preventing cardiovascular diseases comprising administering a TR4 activation inhibitor, and/or wherein the TR4 activation inhibitor wherein inhibits TR4 mediated activation of CD36.

Also disclosed are methods wherein the cardiovascular disease is atherosclerosis, wherein CD36 activation leads to foam cell formation, and/or wherein the TR4 activation inhibitor comprises administering shTR4 RNA.

Also disclosed are methods of reducing foam cell accumulation/atherogenesis comprising interfering with TR4 interaction with the TR4 response element in the CD36 promoter.

Also disclosed are methods wherein reduction of foam cells occurs both in vitro and in vivo.

C. COMPOSITIONS

1. Molecules that Inhibit TR4/Ligand Interactions a) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of TR4 or the genomic DNA of TR4 or they can interact with the polypeptide TR4. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RnaseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than $10^{-6}$. It is more preferred that antisense molecules bind with a $k_d$ less than $10^{-8}$. It is also more preferred that the antisense molecules bind the target molecule with a $k_d$ less than $10^{-10}$. It is also preferred that the antisense molecules bind the target molecule with a $k_d$ less than $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$M. It is preferred that the aptamers bind the target molecule with a $k_d$ less than $10^{-6}$. It is more preferred that the aptamers bind the target molecule with a $k_d$ less than $10^{-8}$. It is also more preferred that the aptamers bind the target molecule with a $k_d$ less than $10^{-10}$. It is also preferred that the aptamers bind the target molecule with a $k_d$ less than $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10 fold lower than the $k_d$ with a background binding molecule. It is more preferred that the aptamer have a $k_d$ with the target molecule at least 100 fold lower than the $k_d$ with a background binding molecule. It is more preferred that the aptamer have a $k_d$ with the target molecule at least 1000 fold lower than the $k_d$ with a background binding molecule. It is preferred that the aptamer have a $k_d$ with the target molecule at least 10000 fold lower than the $k_d$ with a background binding molecule. It is preferred when doing the comparison for a polypeptide for example, that the background molecule be a different polypeptide. For example, when determining the specificity of TR4, TR41 ligand, PPAR, or fragments thereof, aptamers, the background protein could be serum albumin Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616, 466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$. It is more preferred that the triplex forming molecules bind with a $k_d$ less than $10^{-8}$. It is also more preferred that the triplex forming molecules bind the target molecule with a $k_d$ less than $10^{-10}$. It is also preferred that the triplex forming molecules bind the target molecule with a $k_d$ less than $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukaryotic cells. (Yuan et al., *Proc. Natl. Acad. Sci.* USA 89:8006-8010 (1992); WO 93/22434 by Yale; WO 95/24489 by Yale; Yuan and Altman, *EMBO J.* 14:159-168 (1995), and Carrara et al., *Proc. Natl. Acad. Sci.* (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162 b) Antibodies (1) Antibodies Generally

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with TR4 such that TR4 ligand, such as an omega 3 fatty acid, or fragments thereof, such that the interaction between TR4 and the ligand are inhibited or reduced. Antibody also includes, chimeric antibodies and hybrid antibodies, with dual or multiple antigen or epitope specificities, and fragments, such as F(ab')2, Fab', Fab and the like, including hybrid fragments, as well as conjugates of antibody fragments and antigen binding proteins (single chain antibodies) as described, for example, in U.S. Pat. No. 4,704,692, the contents of which are hereby incorporated by reference. Antibodies that bind the disclosed regions of TR4 or fragments thereof, such that TR4 decrease their transactivation activity are also disclosed. The antibodies can be tested for their desired activity using the in vitro assays described herein, or by analogous methods, after which their in vivo therapeutic and/or prophylactic activities are tested according to known clinical testing methods. Thus, fragments of the antibodies that retain the ability to bind their specific antigens are provided. Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

The term "monoclonal antibody" as used herein refers to an antibody obtained from a substantially homogeneous population of antibodies, i.e., the individual antibodies within the population are identical except for possible naturally occurring mutations that can be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., *Proc. Natl. Acad. Sci. USA*, 81:6851-6855 (1984)).

The disclosed monoclonal antibodies can be made using any procedure which produces mono clonal antibodies. For example, monoclonal antibodies of the invention can be prepared using hybridoma methods, such as those described by Kohler and Milstein, *Nature*, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes can be immunized in vitro, e.g., using the binding domains of the compositions described, herein, such as the ligand binding domain, described herein.

The monoclonal antibodies can also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. *Curr. Opin. Biotechnol.* 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods of the invention serves to lessen the chance that an antibody administered to a human will evoke an undesirable immune response.

(2) Human Antibodies

The human antibodies of the invention can be prepared using any technique. Examples of techniques for human monoclonal antibody production include those described by Cole et al. (*Monoclonal Antibodies and Cancer Therapy*, Alan R. Liss, p. 77, 1985) and by Boerner et al. (*J. Immunol.*, 147(1):86-95, 1991). Human antibodies of the invention (and fragments thereof) can also be produced using phage display libraries (Hoogenboom et al., *J. Mol. Biol.*, 227:381, 1991; Marks et al., *J. Mol. Biol.*, 222:581, 1991).

The human antibodies of the invention can also be obtained from transgenic animals. For example, transgenic, mutant mice that are capable of producing a full repertoire of human antibodies, in response to immunization, have been described (see, e.g., Jakobovits et al., *Proc. Natl. Acad. Sci. USA*, 90:2551-255 (1993); Jakobovits et al., *Nature,* 362:255-258 (1993); Bruggermann et al., *Year in Immunol.*, 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

(3) Humanized Antibodies

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies can also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., *Nature*, 321:522-525 (1986), Reichmann et al., *Nature*, 332:323-327 (1988), and Presta, *Curr. Opin. Struct. Biol.*, 2:593-596 (1992)).

Methods for humanizing non-human antibodies are well known in the art. For example, humanized antibodies can be generated according to the methods of Winter and co-workers (Jones et al., *Nature,* 321:522-525 (1986), Riechmann et al., *Nature,* 332:323-327 (1988), Verhoeyen et al., *Science,* 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

(4) Administration of Antibodies

Administration of the antibodies can be done as disclosed herein. Nucleic acid approaches for antibody delivery also exist. The broadly neutralizing antibodies and antibody fragments of the invention can also be administered to patients or subjects as a nucleic acid preparation (e.g., DNA or RNA) that encodes the antibody or antibody fragment, such that the patient's or subject's own cells take up the nucleic acid and produce and secrete the encoded antibody or antibody fragment. The delivery of the nucleic acid can be by any means, as disclosed herein, for example.

c) Compositions Identified by Screening with Disclosed Compositions/Combinatorial Chemistry (1) Combinatorial Chemistry The disclosed compositions can be used as targets for any combinatorial technique to identify molecules or macromolecular molecules that interact with the disclosed compositions in a desired way. The nucleic acids, peptides, and related molecules disclosed herein, such as TR4, PPAR, and/or TR4 ligand or fragments thereof, can be used as targets for the combinatorial approaches. Also disclosed are the compositions that are identified through combinatorial techniques or screening techniques in which the compositions disclosed in herein, such as TR4, PPAR, and/or TR4 ligand or fragments thereof, or portions thereof, are used as the target in a combinatorial or screening protocol.

It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed compositions, such as, TR4, PPAR, and/or TR4 ligand or fragments thereof, or portions thereof, are also disclosed. Thus, the products produced using the combinatorial or screening approaches that involve the disclosed compositions, such as, TR4, PPAR, and/or TR4 ligand or fragments thereof, or portions thereof, are also considered herein disclosed.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 μg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods related to combinatorial chemistry)

A preferred method for isolating proteins that have a given function is described by Roberts and Szostak (Roberts R. W. and Szostak J. W. Proc. Natl. Acad. Sci. USA, 94(23) 12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA, to be translated. In addition, because of the attachment of the puromycin, a peptidyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23) 12997-302 (1997)).

Another preferred method for combinatorial methods designed to isolate peptides is described in Cohen et al. (Cohen B. A., et al., Proc. Natl. Acad. Sci. USA 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that interactions between synthetic or engineered peptide sequences could be identified which bind a molecule of choice. The benefit of this type of technology is that the selection is done in an intracellular environment. The method utilizes a library of peptide molecules that are attached to an acidic activation domain. A peptide of choice, for example a portion of TR4, PPAR, and/or TR4 ligand or fragments thereof, or portions thereof, is attached to a DNA binding domain of a transcriptional activation protein, such as Gal 4. By performing the two-hybrid technique on this type of system, molecules that bind the portion of TR4, PPAR, and/or TR4 ligand or fragments thereof, or portions thereof, can be identified.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972, 719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856, 107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

Screening molecules similar to TR4, PPAR, and/or TR4 ligand or fragments thereof, or portions thereof for inhibition or activation of TR4-ligand interaction or activity or PPAR-TR4 ligand interaction or activity are methods of isolating desired compounds.

As used herein combinatorial methods and libraries included traditional screening methods and libraries as well as methods and libraries used in iterative processes.

It is understood that disclosed are methods using combinatorial libraries, as discussed herein, relating to the knowledge disclosed herein that TR4 has a ligand and that this ligand is omega 3 fatty acid, such as EPA or DHA, as disclosed herein. Furthermore, disclosed are methods which utilize the relationship between TR4, TR4 ligand, and PPAR. Disclosed are strategies for identifying TR4 modulators or PPAR modulators which, for example, interact preferentially with PPAR, or with TR4, and which have interactions related to TR4 ligand, such as omega 3 fatty acids.

(2) Computer Assisted Drug Design

The disclosed compositions can be used as targets for any molecular modeling technique to identify either the structure of the disclosed compositions or to identify potential or actual molecules, such as small molecules, which interact in a desired way with the disclosed compositions. The nucleic acids, peptides, and related molecules disclosed herein can be used as targets in any molecular modeling program or approach.

It is understood that when using the disclosed compositions in modeling techniques, molecules, such as macromolecular molecules, will be identified that have particular desired properties such as inhibition or stimulation or the target molecule's function. The molecules identified and isolated when using the disclosed compositions, such as TR4, and/or fragments thereof, are also disclosed. Thus, the products produced using the molecular modeling approaches that involve the disclosed compositions, such as TR4 and/or fragments thereof, are also considered herein disclosed.

Thus, one way to isolate molecules that bind a molecule of choice is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling, and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 *Acta Pharmaceutica Fennica* 97, 159-166; Ripka, *New Scientist* 54-57 (Jun. 16, 1988); McKinaly and Rossmann, 1989 *Annu. Rev. Pharmacol. Toxiciol.* 29, 111-122; Perry and Davies, *QSAR: Quantitative Structure-Activity Relationships in Drug Design* pp. 189-193 (Alan R. Liss, Inc. 1989); Lewis and Dean, 1989 *Proc. R. Soc. Lond.* 236, 125-140 and 141- 162; and, with respect to a model enzyme for nucleic acid components, Askew, et al., 1989 *J. Am. Chem. Soc.* 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of molecules specifically interacting with specific regions of DNA or RNA, once that region is identified.

Although described above with reference to design and generation of compounds which could alter binding, one could also screen libraries of known compounds, including natural products or synthetic chemicals, and biologically active materials, including proteins, for compounds which alter substrate binding or enzymatic activity.

d) Methods of Identifying Modulators of TR4 Ligand Interaction

Disclosed are methods of identifying modulators of TR4 ligand interaction, comprising incubating a library of molecules with TR4 forming a mixture, and identifying the molecules that reduce an interaction between TR4 and TR4 ligand. Also disclosed are methods wherein the TR4 ligand is an omega 3 fatty acid, such as disclosed herein.

Also disclosed are compositions produced by any of the processes as disclosed herein, as well as compositions capable of being identified by the processes disclosed herein.

Also disclosed are methods of identifying activators of TR4 transcription activity comprising, a) administering a composition to a system, wherein the system supports TR4 transcription activity, b) assaying the effect of the composition on the amount of TR4 transcription activity in the system, and c) selecting a composition which causes an increase in the amount of TR4 transcription activity present in the system relative to the system without the addition of the composition, wherein the methods comprise comparing the activity to the activity of an omega 3 fatty acid.

2. Aspects Applicable to all Compositions a) Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least, about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment. It is understood that any of the methods typically can be used and that in certain instances the results of these various methods can differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

b) Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions can provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

c) Nucleic Acids

There are a variety of molecules disclosed herein that are nucleic acid based, including for example the nucleic acids that encode, for example TR4 and/or fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

(1) Nucleotides and Related Molecules

A nucleotide is a molecule that contains a base moiety, a sugar moiety, and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. A non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

(2) Sequences

There are a variety of sequences related to the genes of TR4 or PPAR, and/or fragments, which can be found at Genbank, at for example, http://www.pubmed.gov and these sequences and others are herein incorporated by reference in their entireties as well as for individual subsequences contained therein.

The disclosed sequences and variants can be founding Genbank. It is understood that the description related to this sequence is applicable to any sequence unless specifically indicated otherwise. Those of skill in the art understand how to resolve sequence discrepancies and differences and to adjust the compositions and methods relating to a particular sequence to other related sequences. Primers and/or probes can be designed for any sequence given the information disclosed herein and known in the art.

(3) Primers and Probes

Disclosed are compositions including primers and probes, which are capable of interacting with the TR4 or PPAR nucleic acids as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the TR4 or PPAR and/or fragments thereof, nucleic acid or region of the TR4 or PPAR and/or fragments thereof, nucleic acid or they hybridize with the complement of the TR4 or PPAR and/or fragments thereof nucleic acid or complement of a region of the TR4 or PPAR and/or fragments thereof nucleic acid.

d) Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

(1) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as nucleic acids encoding TR4 or PPAR and/or fragments thereof into the cell without degradation and may include, for example, a promoter yielding expression of the gene in the cells into which it is delivered. In some embodiments the vectors are derived from either a virus or a retrovirus. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone, as well as lentiviruses. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(a) Retroviral Vectors

A retrovirus is a virus belonging to the virus family of Retroviridae, including any types, subfamilies, genus, or tropisms. Retroviral vectors, in general, are described by Verma, 1M, Retroviral vectors for gene transfer. In Microbiology-1985, American Society for Microbiology, p. 229-32, Washington, (1985), which is incorporated by reference herein.

Examples of methods using retroviral vectors for gene therapy are described in U.S. Pat. Nos. 4,868,116 and 4,980,286; PCT applications WO 90/02806 and WO 89/07136; and Mulligan (1993) Science 260:926-32; the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(b) Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virions are generated in a cell line such as the human 293 cell line. In another preferred embodiment both the E1 and E3 genes are removed from the adenovirus genome.

(c) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The vectors of the present invention thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

(d) Large Payload Viral Vectors

189. Molecular genetic experiments with large human herpes viruses have provided a means whereby large heterologous DNA fragments can be cloned, propagated and established in cells permissive for infection with herpes viruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

(2) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed compositions or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Feigner et al. *Proc. Natl. Acad. Sci. USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.,* 35:421-425, (1992); Pietersz and McKenzie, *Immunol. Rev.,* 129:57-80, (1992); and Roffler, et al., *Biochem. Pharmacol,* 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochim et Biophys. Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

(3) In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

e) Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

(1) Viral Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature*, 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell. Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell. Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promoter and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

(2) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker can be a selectable marker. Examples of suitable selectable markers for mammalian cells are dihydrofolate reductase (DHFR), thymidine kinase, neomycin, neomycin analog G418, hygromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

f) Peptides (1) Protein Variants

As discussed herein there are numerous variants of the TR4 or PPAR proteins and/or fragments thereof that are known and herein contemplated. In addition, to the known functional TR4 or PPAR and/or fragments thereof species homologs there are derivatives of the TR4 or PPAR proteins and/or fragments thereof, which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

| Amino Acid Abbreviations | |
|---|---|
| Amino Acid | Abbreviations |
| alanine | AlaA |
| allosoleucine | Aile |
| arginine | ArgR |
| asparagine | AsnN |
| aspartic acid | AspD |
| cysteine | CysC |
| glutamic acid | GluE |
| glutamine | GlnK |
| glycine | GlyG |
| histidine | HisH |
| isolelucine | IleI |
| leucine | LeuL |
| lysine | LysK |
| phenylalanine | PheF |
| proline | ProP |
| pyroglutamic acid | Glu |
| serine | SerS |
| threonine | ThrT |
| tyrosine | TyrY |
| tryptophan | TrpW |
| valine | ValV |

TABLE 2

Amino Acid Substitutions

| Original Residue | Exemplary Conservative Substitutions, others are known in the art. |
|---|---|
| Ala | ser |
| Arg | lys, gln |
| Asn | gln; his |
| Asp | glu |
| Cys | ser |
| Gln | asn, lys |
| Glu | asp |
| Gly | pro |
| His | asn; gln |
| Ile | leu; val |
| Leu | ile; val |
| Lys | arg; gln; |
| Met | Leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also can be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W.H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence can not be written out herein, it is understood that each and every sequence is in fact disclosed and described herein through the disclosed protein sequence. It is also understood that while no amino acid sequence indicates what particular DNA sequence encodes that protein within an organism, where particular variants of a disclosed protein are disclosed herein, the known nucleic acid sequence that encodes that protein in the particular organism from which that protein arises is also known and herein disclosed and described.

g) Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions can be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

(1) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers can be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The pharmaceutical composition can be administered in a number of ways depending on whether local or systemic treatment is desired, and on the area to be treated. Administration can be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration include powders or granules, suspensions or solutions in water or non-aqueous media, capsules, sachets, or tablets. Thickeners, flavorings, diluents, emulsifiers, dispersing aids or binders can be desirable.

Some of the compositions can potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

(2) Therapeutic Uses

Effective dosages and schedules for administering the compositions can be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as an antibody or other molecule, such as fragment of TR4 or PPAR, for forming or mimicking a TR4/ligand, for example, the efficacy of the therapeutic antibody or fragment can be assessed in various ways well known to the skilled practitioner. For instance, one of ordinary skill in the art will understand that a composition, such as an antibody or fragment, disclosed herein is efficacious in forming or mimicking a TR4 ligand interaction in a subject by observing, for example, that the composition reduces the amount of TR4 ligand binding or TR4 activity. The TR4 activity can be measured using assays as disclosed herein or known in the art, and the TR4 ligand binding can be assayed in numerous ways disclosed herein or known in the art. Any change in activity is disclosed, but a 5%, 10%, 15%, 20%, 25%, 30%, 35%, 40%, 45%, 50%, 55%, 60%, 65%, 70%, 75%, 80%, 90%, or a 95% reduction in TR4 or PPAR activity are also disclosed.

Other molecules that interact with TR4 or PPAR which do not have a specific pharmaceutical function, but which can be used for tracking changes within cellular chromosomes or for the delivery of diagnostic tools for example can be delivered in ways similar to those described for the pharmaceutical products, and which, for example, modulate the interaction of a TR4 ligand.

The disclosed compositions and methods can also be used for example as tools to isolate and test new drug candidates for a variety of PPAR and TR4 related diseases such as those associated with diabetes and cardiovascular disease, and in particular diseases where modulation of PPAR or TR4 differentially relative to each other, such as diabetes, is preferred.

h) Chips and Micro Arrays

Disclosed are chips where at least one address is the sequences or part of the sequences set forth in any of the nucleic acid sequences disclosed herein. Also disclosed are chips where at least one address is the sequences or portion of sequences set forth in any of the peptide sequences disclosed herein.

Also disclosed are chips where at least one address is a variant of the sequences or part of the sequences set forth in any of the nucleic acid sequences disclosed herein. Also disclosed are chips where at least one address is a variant of the sequences or portion of sequences set forth in any of the peptide sequences disclosed herein.

i) Computer Readable Mediums

It is understood that the disclosed nucleic acids and proteins can be represented as a sequence consisting of the nucleotides of amino acids. There are a variety of ways to display these sequences, for example the nucleotide guanosine can be represented by G or g. Likewise the amino acid valine can be represented by Val or V. Those of skill in the art understand how to display and express any nucleic acid or protein sequence in any of the variety of ways that exist, each of which is considered herein disclosed. Specifically contemplated herein is the display of these sequences on computer readable mediums, such as, commercially available floppy disks, tapes, chips, hard drives, compact disks, and video disks, or other computer readable mediums. Also disclosed are the binary code representations of the disclosed sequences. Those of skill in the art understand what computer readable mediums. Thus, computer readable mediums on which the nucleic acids or protein sequences are recorded, stored, or saved.

Disclosed are computer readable mediums comprising the sequences and information regarding the sequences set forth herein.

3. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended.

D. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323-356 (1984), (phosphotriester and phosphite-triester methods), and Narang et al., *Methods Enzymol.*, 65:610-620 (1980), (phosphotriester method). Protein nucleic acid molecules can be made using known methods such as those described by Nielsen et al., *Bioconjug. Chem.* 5:3-7 (1994).

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

3. Process for Making the Compositions

Disclosed are processes for making the compositions as well as making the intermediates leading to the compositions. There are a variety of methods that can be used for making these compositions, such as synthetic chemical methods and standard molecular biology methods. It is understood that the methods of making these and the other disclosed compositions are specifically disclosed.

Disclosed are cells produced by the process of transforming the cell with any of the disclosed nucleic acids. Disclosed are cells produced by the process of transforming the cell with any of the non-naturally occurring disclosed nucleic acids.

Disclosed are any of the disclosed peptides produced by the process of expressing any of the disclosed nucleic acids. Disclosed are any of the non-naturally occurring disclosed peptides produced by the process of expressing any of the disclosed nucleic acids. Disclosed are any of the disclosed peptides produced by the process of expressing any of the non-naturally disclosed nucleic acids.

Disclosed are animals produced by the process of transfecting a cell within the animal with any of the nucleic acid molecules disclosed herein. Disclosed are animals produced by the process of transfecting a cell within the animal any of the nucleic acid molecules disclosed herein, wherein the animal is a mammal. Also disclosed are animals produced by the process of transfecting a cell within the animal any of the nucleic acid molecules disclosed herein, wherein the mammal is mouse, rat, rabbit, cow, sheep, pig, or primate including a human, ape, monkey, orangutan, or chimpanzee.

Also disclosed are animals produced by the process of adding to the animal any of the cells disclosed herein.

Also disclosed are process for purifying and extracting omega 3 fatty acids, such as those obtained from fish oil.

E. METHODS OF USING THE COMPOSITIONS

1. Methods of Using the Compositions as Research Tools

The compositions can be used for example as targets in combinatorial chemistry protocols or other screening protocols to isolate molecules that possess desired functional properties related to TR4 and TR4 ligand. For example, TR4 and its ligand interaction domains can be used in procedures that will allow the isolation of molecules or small molecules that mimic their binding properties. Libraries of molecules can be screened for interaction with TR4 by incubating the potential binding molecules which compete with omega 3 fatty acids for TR4 binding, and then isolating those that are specifically active. There are many variations to this general protocol.

The disclosed compositions can also be used diagnostic tools related to diseases such as diabetes or cardiovascular disease.

The disclosed compositions can be used as discussed herein as either reagents in micro arrays or as reagents to probe or analyze existing microarrays. The disclosed compositions can be used in any known method for isolating or identifying single nucleotide polymorphisms. The compositions can also be used in any known method of screening assays, related to chip/micro arrays. The compositions can also be used in any known way of using the computer readable embodiments of the disclosed compositions, for example, to study relatedness or to perform molecular modeling analysis related to the disclosed compositions.

F. EXAMPLES

1. Example 1

Polyunsaturated Fatty Acid Metabolites and TZD Activate TR4-Mediated CD36 Expression and Foam Cell Formation a) Results (1) TR4 Plays a Vital Role in Foam Cell Formation.

A pathophysiological role for TR4 in cardiovascular diseases such as atherosclerosis, was shown by TR4's involvement in foam cell formation, a critical step in atherogenesis. Peritoneal macrophages isolated from $TR4^{-/-}$ and wild type TR4 control ($TR^{+/+}$) mice were treated with 100 μg/ml oxLDL for 24 h. Microscopic examination of these macrophages revealed a significant accumulation of oil red O-positive droplets in $TR4^{+/+}$ macrophages, indicative of lipid accumulation. In contrast, little or no oil red O staining was observed in $TR4^{-/-}$ macrophages. Typical data from 2 pairs of $TR4^{-/-}$ vs. $TR4^{+/+}$ mice were presented in FIG. 1A. This reduction of foam cell formation in $TR4^{-/-}$, as compared to $TR4^{+/+}$ macrophages indicates the presence of TR4 is critical for foam cell formation.

Figure 1B:
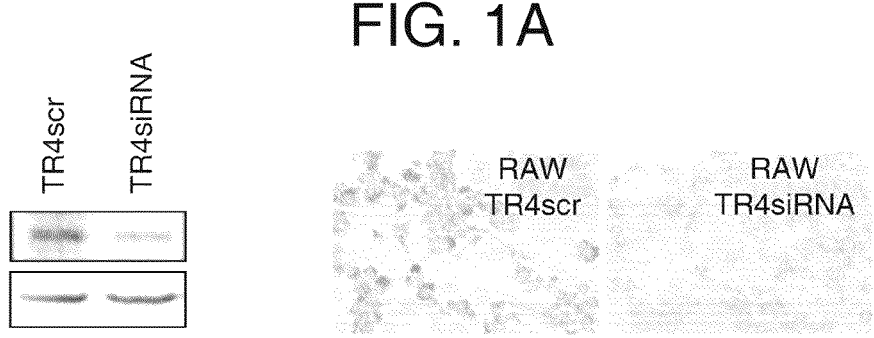
Figure 1C:

Further confirmation of TR4's role in foam cell formation was shown by modulating TR4 expression levels in RAW 264.7 (RAW) macrophage cells by either overexpression of functional TR4cDNA or knockdown of TR4 by si-RNA interfering. These TR4-modulated RAW cells were treated with oxLDL for 24 h after depletion of lipids, and foam cell formation ability was compared. Consistent with the in vivo observation, oil red 0 staining revealed that knockdown of TR4 expression (TR4siRNA) resulted in significant reduction of foam cell formation compared to scramble control (TR4src) (FIG. 1B). In contrast, overexpression of TR4 enhanced foam cell formation in RAW cells (FIG. 1C). Together, the in vivo data from TR4−/− mice (FIG. 1A) and in vitro data from RAW cells transfected with TR4-siRNA (FIG. 1B), or functional TR4 cDNA (FIG. 1C) indicate that TR4 plays a vital role in foam cell formation.

(2) TR4 Promotes the Scavenger Receptor CD36 at the mRNA and Protein Levels.

Figure 2A:
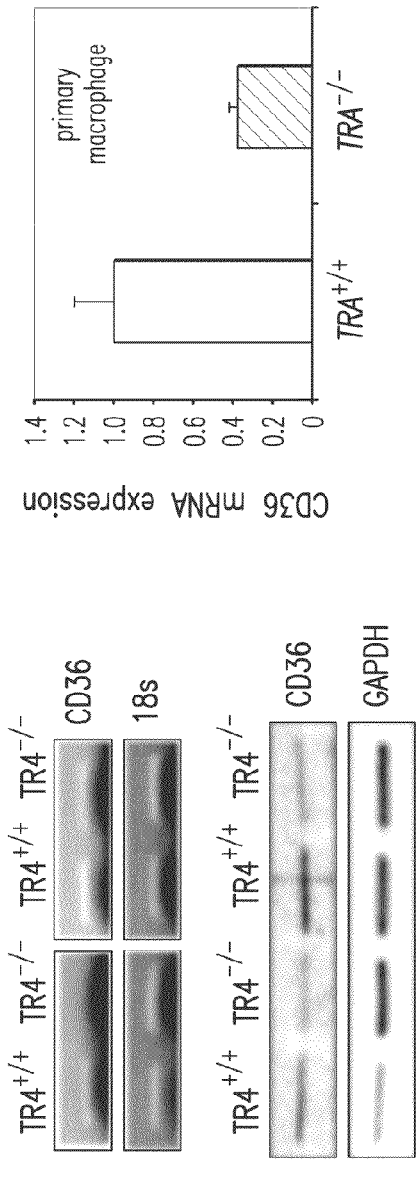
FIGS. 2A, 2B, 2C and 2D show that TR4 modulates CD36 expression.

TR4 modulates CD36, an essential player in foam cell formation. CD36 is mainly responsible for the uptake of oxLDL in macrophages. Wild type murine macrophages express abundant CD36 mRNA and proteins. Peritoneal macrophages from TR4+/+ and TR4−/− mice were used to examine CD36 gene expression in response to the knockout of endogenous TR4 expression. By using semi-quantitative PCR, real-time quantitative PCR, and Western blotting analysis, CD36 mRNA and protein expression in peritoneal macrophages isolated from TR4−/− mice were determined to be significantly lower as compared to those from TR4+/+ mice (FIG. 2A).

Figure 2B:
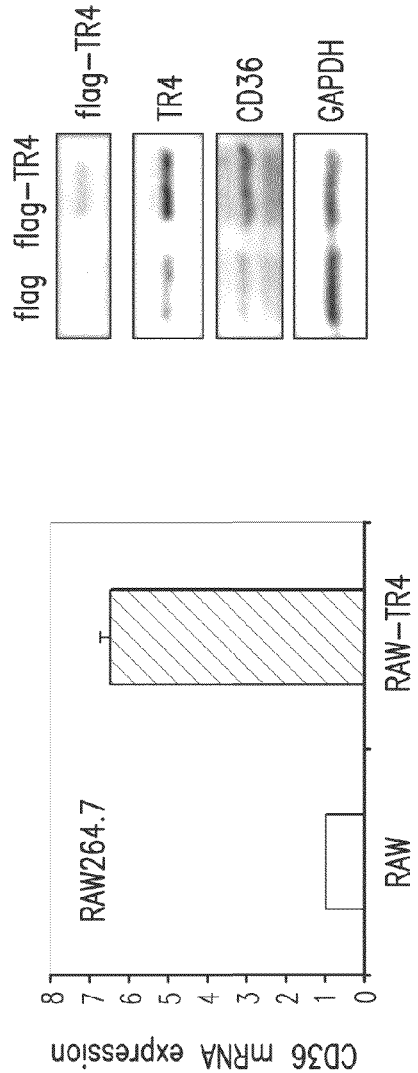
Figure 2C:
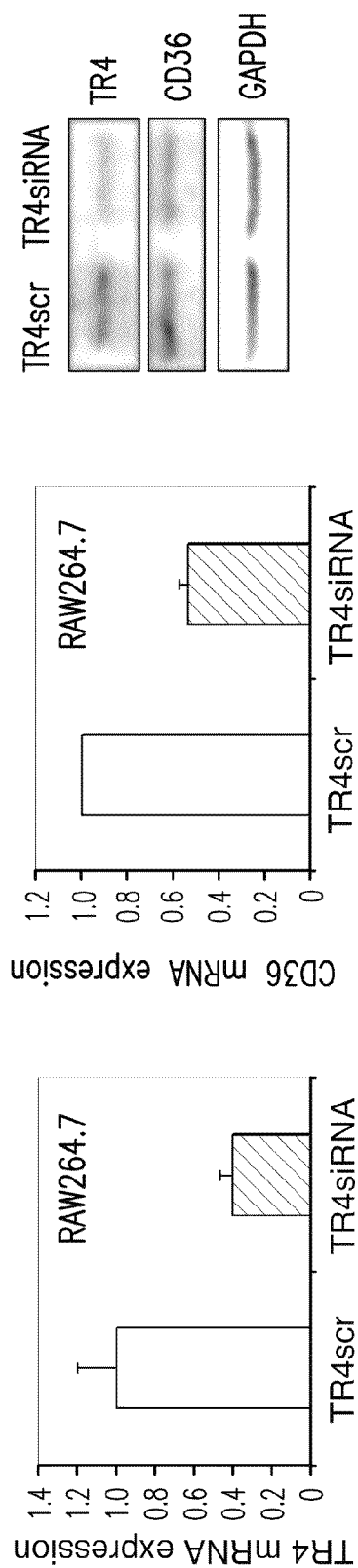

The up-regulation of CD36 by TR4 was confirmed by using established RAW stable cell lines that express functional TR4 cDNA or retroviral-mediated siRNA against TR4. As shown in FIG. 2B, transfection of TR4 increases CD36 expression at both mRNA (FIG. 2B, left panel) and protein (FIG. 2B, right panel) levels. In contrast, knockdown of TR4 reduces CD36 gene expression at both mRNA (FIG. 2C, middle panel) and protein (FIG. 2C, right panel) levels.

Figure 2D:
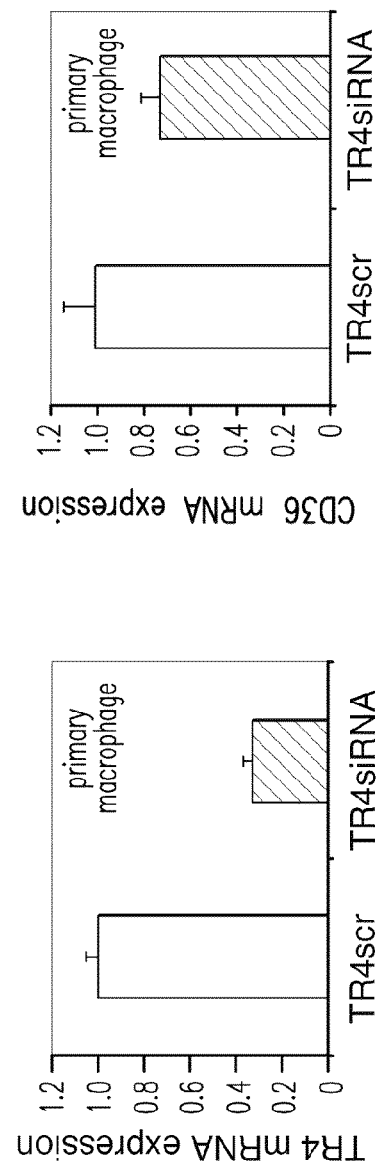

TR4+/+ mice primary peritoneal macrophages with TR4 knocked down via lentiviral-mediated TR4-siRNA were used to avoid the indirect effects of CD36 reduction from the total TR4 knockout mice macrophage. The results showed decreasing TR4 (via TR4-siRNA) in peritoneal macrophages resulted in reduction of CD36 gene expression (FIG. 2D). Together, both in vivo data from TR4−/− mice and in vitro data from RAW cells or primary macrophages transfected with either TR4-siRNA or functional TR4 cDNA all indicate that TR4 can regulate CD36 expression at both mRNA and protein levels.

(3) TR4 Influences Foam Cell Formation Via Modulation of CD36 Expression.

Figure 3A:
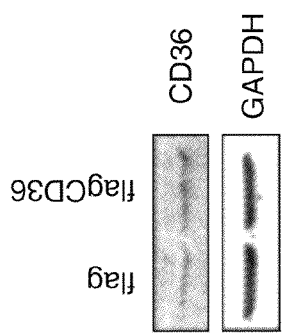
FIGS. 3A and 3B show that CD36 rescues TR4-mediated reduced foam cell formation.
Figure 3B:
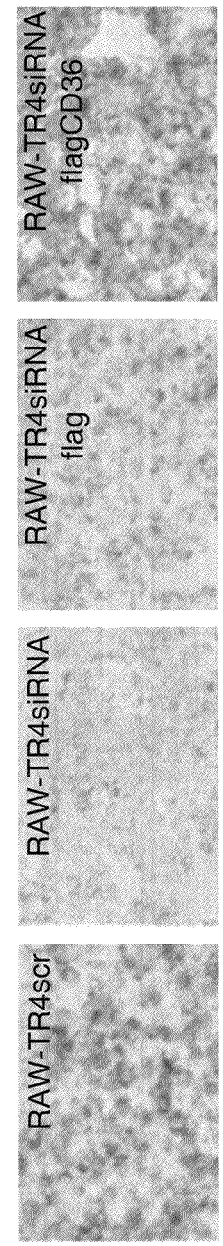

To investigate whether TR4 promoting foam cell formation is via regulating CD36, functional CD36 cDNA was restored, via retroviral transduction, in the Raw-TR4-siRNA cells. As shown in FIG. 3A, transduction of functional CD36 cDNA resulted in increased CD36 protein expression in stable RAW-TR4-siRNA cells. Furthermore, this increased CD36 expression also resulted in the reversion of reduced foam cell formation caused by knockdown of TR4 via TR4-siRNA (FIG. 3B). These results from FIG. 3 clearly demonstrated that TR4 influences foam cell formation via modulation of CD36 expression.

(4) TR4 Modulates CD36 Expression at Transcriptional Level.

Figure 4A:
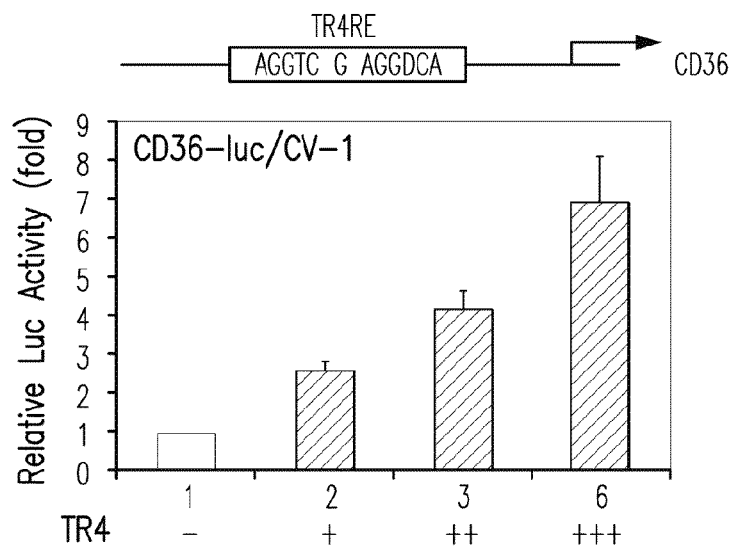
FIGS. 4A, 4B, and 4C show that TR4 promotes CD36 promoter activity via TR4RE.
Figure 4B:
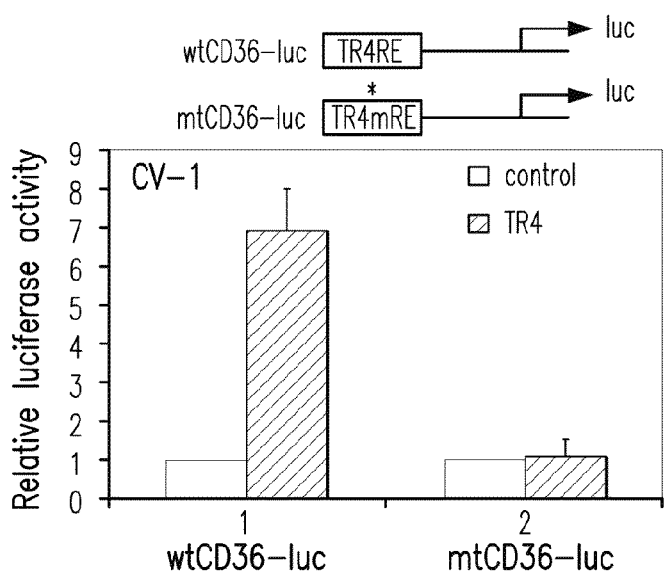
Figure 4C:
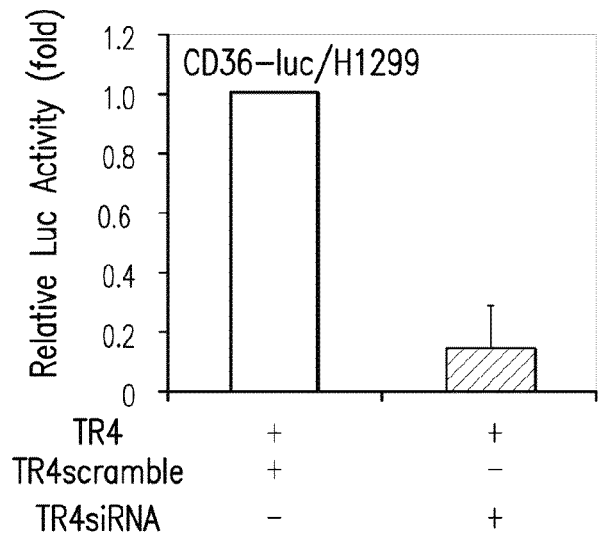

TR4 is a transcriptional factor which can regulate its target gene expression via binding to TR4 responsive element (TR4RE) located in the gene promoter region. TR4 was shown to directly regulate CD36 gene expression at the transcriptional level. The CD36 promoter contains a putative TR4RE, with the sequence of 5'-TGGCCTCTGACTT-3' (SEQ ID NO:6), which could be also bound by PPAR/RXR (Tontonoz et al. Cell, 1998). A 300-bp CD36 5' promoter, which contains TR4RE, was linked to a luciferase reporter and tested. As shown in FIG. 4A, TR4 enhanced CD36 5' promoter activity in a dose-dependent manner. Furthermore, TR4 failed to activate the mutated CD36 promoter activity that replaced functional TR4RE with mutated TR4RE (5'-TG AAACTGACTT) (SEQ ID NO:7) (Tontonoz et al. Cell, 1998), indicating this TR4RE is indeed a TR4 binding site (FIG. 4B). Moreover, retrovirus-based siRNA against TR4 reversed the CD36 5' promoter activity induced by TR4 (FIG. 4C).

(5) TR4 Binds to CD36 5' Promoter In Vivo.

Figure 5A:
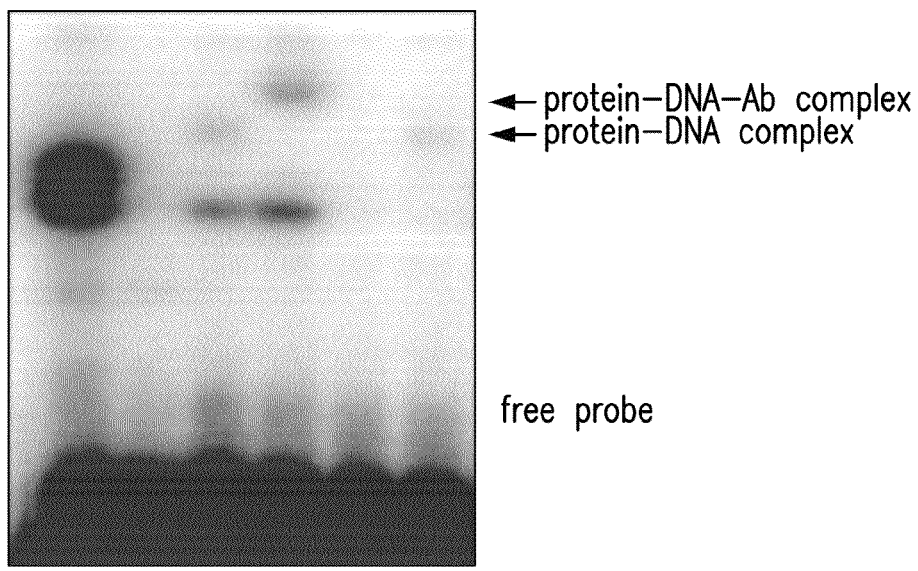
FIGS. 5A and 5B show direct binding of TR4 to the TR4RE site of the CD36 promoter region.
Figure 5B:
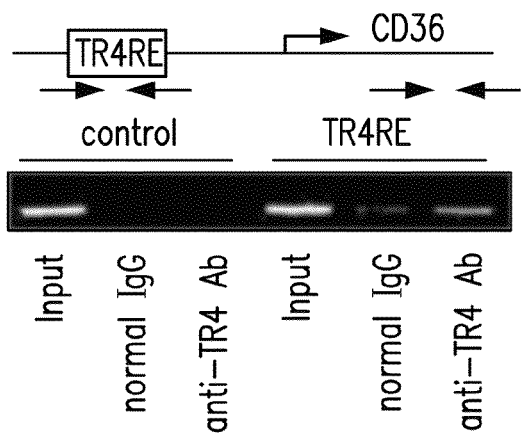

EMSA and ChIP assays showed a physical interaction between TR4 and TR4RE in vitro and in vivo. As shown in FIG. 5A, incubation of $^{32}P$ labeled TR4RE with in vitro transcribed/translated TR4 proteins yielded a slowly migrating band, indicated as protein-DNA complex (lane 3), and adding an anti-TR4antibody resulted in a supershift band (lane 4). This specific band formed by TR4-DNA complex can be competed with excess amount of TR4RE, but not mutant TR4RE competitor (FIG. 5A, lane 5-6), which further proved the specific binding between TR4 and TR4RE. Next, we performed ChIP assays to determine whether TR4 was able to bind to the endogenous CD36 promoter. DNA-protein complexes in the RAW cells were cross-linked in situ, and the chromatin was isolated and sheared. Subsequently, the chromatin was immunoprecipitated with the anti-TR4 antibody, and the DNA was purified and subjected to PCR using CD36 promoter-specific primers. As shown in FIG. 5B, this primer set specifically amplified a fragment of the predicted size, and adding anti-TR4 antibody caused more than a 4-fold up-regulation (FIG. 5B), indicating that this transcription factor indeed is bound in vivo to the regulatory portion of the CD36 gene. Taken together, both EMSA and ChIP assays indicate that TR4 induces CD36 expression by binding directly to the CD36 promoter region.

(6) PUFA Metabolites and TZD Activate TR4-Mediated CD36 Transactivation.

Figure 6A:
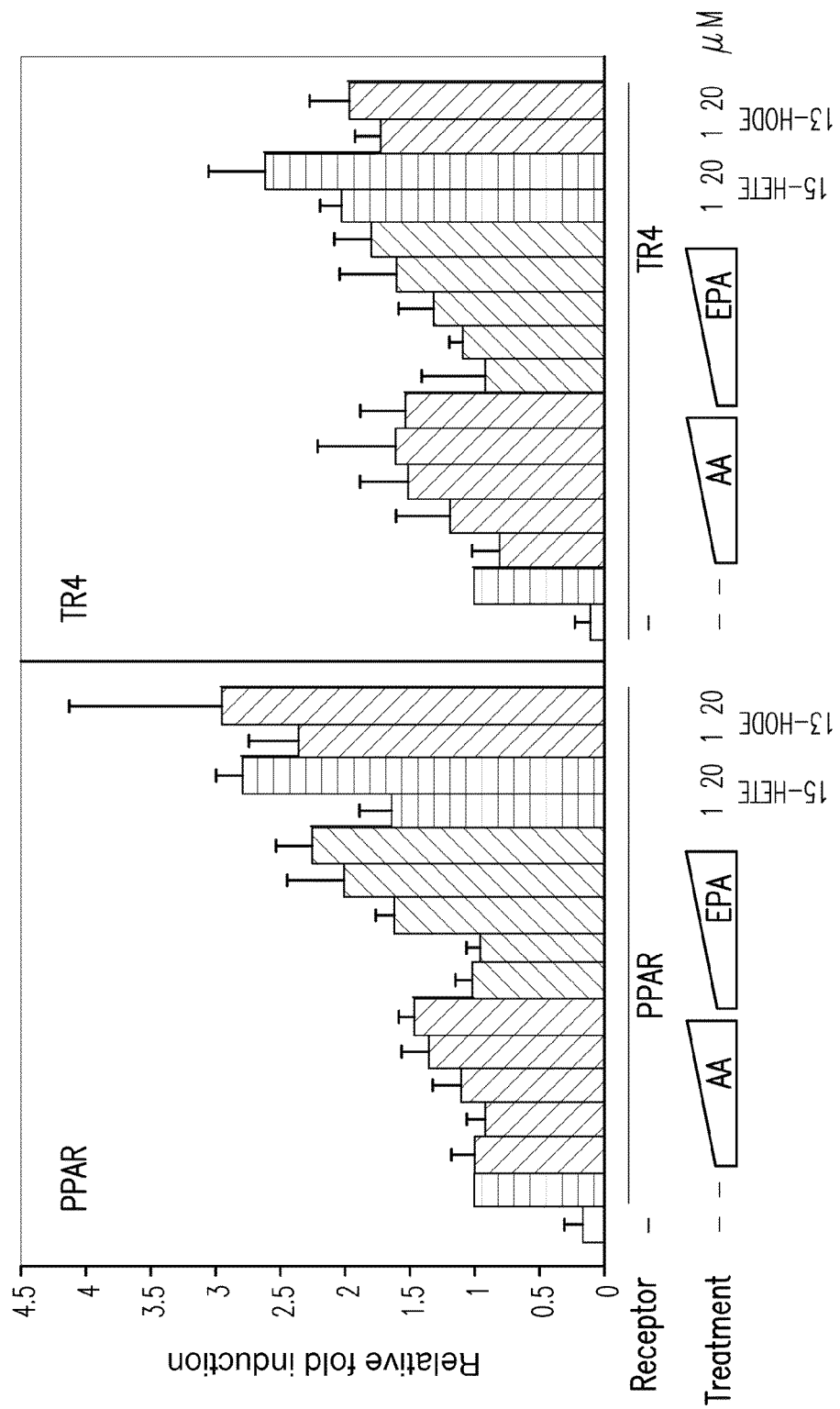
FIGS. 6A, 6B and 6C show that PUFAs metabolites and rosiglitazone act as activators/ligands for TR4.

In addition to TR4, another member of the nuclear receptor superfamily, PPAR, was also reported to be able to modulate CD36 expression (Tontonoz et al. Cell, 1998). Early studies demonstrated that several CD36 upstream activators, such as cytokines (TNF, IFN-r and IL-13), PUFAs [arachidonic acid (AA), linoleic acid (LA), docosahexaenoic (DHA) and eicosapentaenoic (EPA)], PUFA metabolites (15-HETE and 13-HODE), TZD (rosiglitazone/BRL 49653), and 15-deoxy-1-prostaglandin J2 (15d-J2) were able to modulate CD36 expression via activation of PPAR. These activators/ligands were shown also to modulate CD36 expression via activation of TR4. As shown in FIG. 6A, AA and EPA, from 1-250 M, mildly induced TR4-mediated as well as PPAR/RXR-mediated CD36 expression. Interestingly, the PUFA metabolites, including 15-HETE and 13-HODE, showed much better induction for both TR4- and PPAR/RXR-mediated CD36 expression.

Figure 6B:
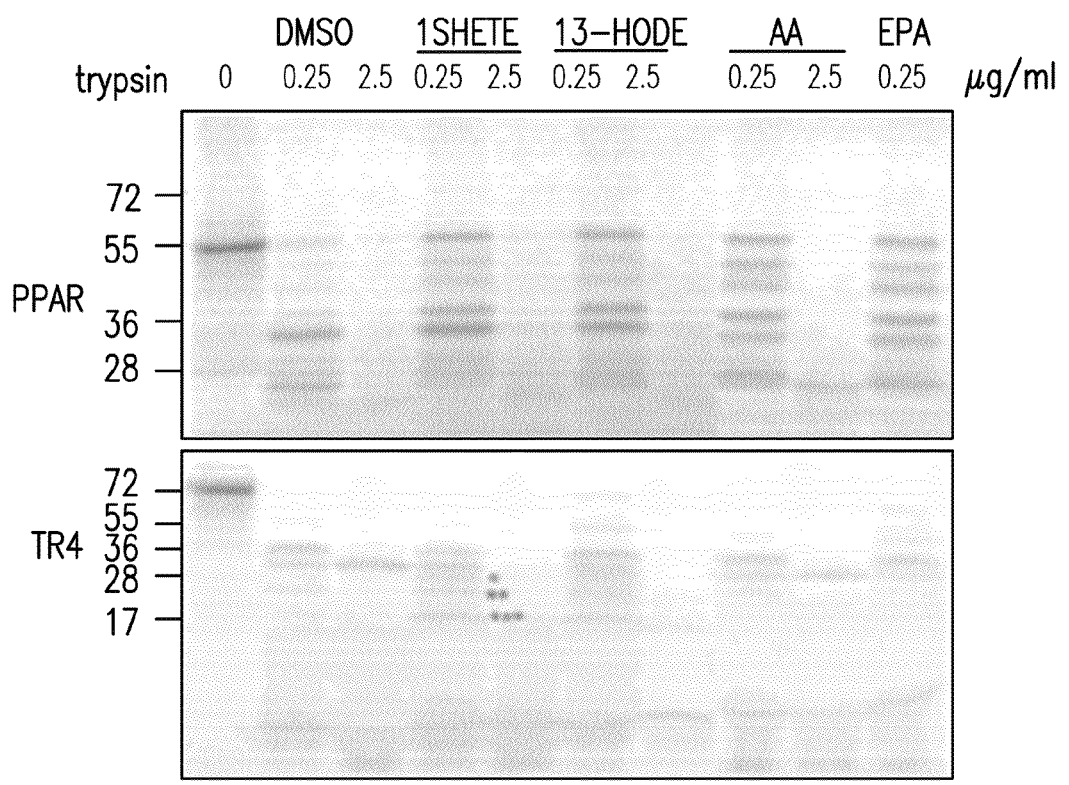

A limited proteolysis assay further confirmed PUFAs and their metabolites could activate TR4 or PPAR via direct binding to receptor with conformational changes. As shown in FIG. 6B, 15-HETE-bound TR4 and 13-HODE-bound TR4, as well as 15-HETE-bound-PPAR and 13-HODE-bound PPAR display several changed proteolysis resisting fragments (labeled with *) as compared to DMSO control. The TR4 distinct conformational alterations upon binding to PUFA metabolites indicated that these PUFA metabolites might act as endogenous ligands for PPAR (Forman et al. PNAS, 1997; Kliewer et al. PNAS, 1997, Xu et al. Mol Cell, 1999) as well as TR4.

Figure 6C:
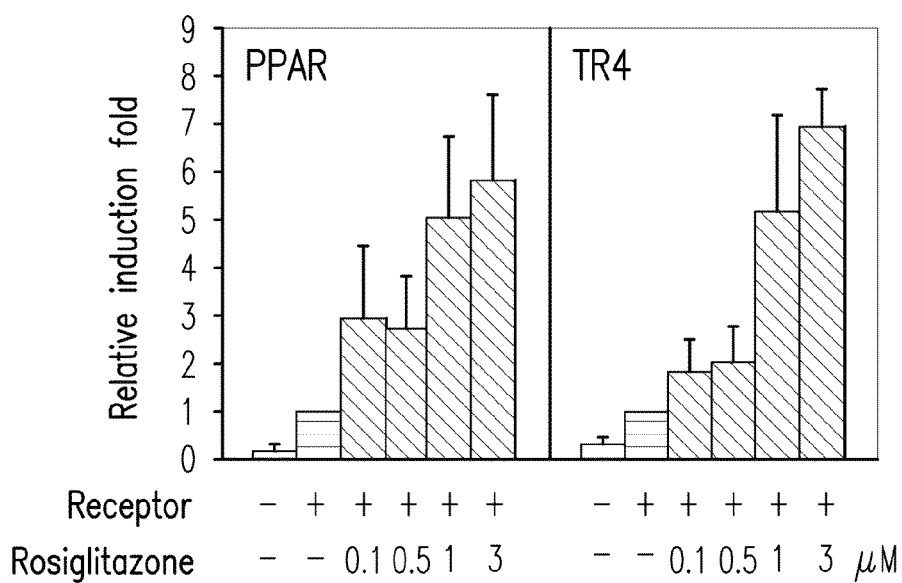

TZD, a drug for treating type II diabetes, is a synthetic PPAR ligand with better binding affinity to PPAR that results in a stronger induction of CD36 expression (Lehmann et al. J Biol Chem, 1995). As expected, rosiglitazone, a TZD, strongly promotes TR4-induced CD36 transactivation (FIG. 6C) Similar induction was also found when we replaced TR4 with PPAR/RXR (FIG. 6C). Together, results from FIG. 6 demonstrate that PUFA metabolites and TZD can function as ligands/activators for TR4 (and PPAR), which indicates TR4, like PPAR, is a novel fatty acid regulator that may play vital roles in metabolism syndrome, diabetes, and cardiovascular diseases.

b) Discussion

Demonstrated herein is a novel role for TR4 in foam cell formation/atherosclerosis via regulation of CD36. TR4 functions as a transcriptional factor that directly binds to the CD36 promoter and regulates CD36 gene expression in macrophage cells. Over-expression of CD36 in the TR4 knockdown macrophages can restore foam cell formation reduction, indicating that CD36 is involved in TR4-mediated foam cell formation. Interestingly, the TR4 binding site in the CD36 promoter is the same as PPARγ which controls CD36 gene expression and foam cell formation (Castrillo and Tontonoz J Clin Invest, 2004; Joseph and Tontonoz Curr Opin Pharmacol, 2003; Beaven and Tontonoz Annu Rev Med, 2006; Li et al. J Clin Invest, 2000; Ricote et al. Nature, 1998). However, a significant change in PPARγ gene expression levels in TR4−/− mouse macrophages was not observed (data not shown), indicating that PPARγ-CD36 signaling is not able to compensate or rescue the TR4-CD36 signaling.

During screening of CD36 upstream activators identified some PPARγ ligands/activators as stimulators of TR4-mediated CD36 expression to different levels, which uncovered a selective array of ligands/activators between TR4 and PPARs with different potency to activate their downstream target genes. Since both TR4 and PPARs recognize similar DNA responsive elements, it is important to identify distinct ligands/activators that can differentially activate their own distinct target genes and therefore result in different effects on cardiovascular diseases and diabetes.

Promotion of foam cell formation via activation of TR4-CD36 signaling can promote atherosclerosis/cardiovascular disease. The fact that this TR4-CD36 transactivation can be further induced by TZD, an anti-diabetes drug, indicates conflicting roles of TZD in its effect on cardiovascular disease vs diabetes (Nissen and Wolski N Engl J Med, 2007; Yki-Jarvinen N Engl J Med, 2004). Further investigation of TR4 roles in vivo, especially in myocardial cells, would be of interest to uncover the complexity of TR4 in regulating lipid metabolism in different tissues under normal physiological and pathological processes.

A critical role for the nuclear receptor TR4 in foam cell formation/cardiovascular diseases through regulation of CD36 expression has been identified. More importantly, TR4 transactivation can be further promoted via its ligands/activators, such as PUFA metabolites and TZD, indicating TR4 is a new potential therapeutic target for the battle of TR4-mediated lipid metabolism syndromes.

c) Materials and Methods (1) Mouse Studies

All animal experimental protocols described here were approved by the University Committee on Animal Resources and the office of Environmental Health and Safety before implementation. The TR4 heterozygous (TR4$^{+/-}$) mice were intercrossed to generate TR4$^{-/-}$ mice. TR4$^{+/-}$ mice on C57BL/6×129SvEv background were collaborated from Lexicon Genetics Incorporated (Collins et al. PNAS, 2004).

(2) Isolation of Mouse Peritoneal Macrophages

Mice were peritoneally injected with 3 ml of 4% thioglycolate broth media. Four days later, thioglycolate-elicited peritoneal macrophages were isolated, seeded with RPMI medium supplemented with 8% fetal bovine serum, and purified by 2 h adherence.

(3) Oil Red O Staining of Foam Cells

Macrophages were seeded on 96-well plates overnight and cultured in lipid-depleted medium for 1 day, and then treated with oxLDL (8 g/ml or 100 g/ml) for 24 h. After washing with PBS, the cells were fixed with 3.7% formaldehyde for 2 min, followed by stained with fresh 0.5% oil red 0 for 2 h. oxLDL was purchased from Intracel (Frederick, Md.).

(4) Analysis of Atherosclerosis

Aortas were collected and stained by Sudan IV, as described previously (Palinski et al. Arterioscler, 1994). The extent of atherosclerosis in en face mouse aorta was quantified using photoshop software (Adobe, USA) (Lehr et al. Circulation, 2001).

(5) Cell Culture, Transient Transfection and Luciferase Assay

Mouse macrophage RAW 264.7 cells, obtained from ATCC, were cultured in DMEM medium supplemented with 8% fetal bovine serum and 100 g/ml penicillin-streptomycin and maintained on the petri-dishes. For the CD36-luc assay, cells (CV-1 and H1299) were seeded in 24-well plates, reporter plasmids were co-transfected with TR4 or PPAR/RXR, and then treated with BSA-PUFAs (AA and EPA) (Wang et al. Am J Physiol, 1997), their metabolites (13-

HODE and 15-HETE in DMSO) and TZD (rosiglitazone/ BRL 49653). After 24 h, cells were harvested for luciferase assays.

(6) Real-Time RT-PCR

Real-time RT-PCR was performed as described previously (Yang et al. Biochem Biophsy Res Commun, 2004). Briefly, cells were harvested and RNA was isolated by Trizol (Invitrogen, CA) and then reverse transcribed by Superscript III (Invitrogen) according to the manual instructions. Realtime PCR was applied using SYBR green PCR mix (Qiagen). Each sample was run in triplicate. Data were analyzed by an iCycler iQ software (Biorad, CA).

(7) Western Blot Analysis

Western blot analysis was performed as described previously (Xie et al. Prostate, 2004). Anti-GAPDH and anti-CD36 antibodies were from Santa Cruz. Anti-flag M2 monoclonal antibody was purchased from Sigma and anti-TR4 antibody was produced as previously reported (Collins et al. PNAS, 2004).

(8) DNA Constructs

Full length CD36 were isolated from cDNA of mouse RAW264.7 cells and then subcloned into pCDNA3-flag. Mouse CD36-promoter-300, and mtCD36-promoter were amplified from genomic DNA of RAW264.7 cells by PCR and subcloned into pGL3-basic vector. TR4 was amplified from pCMX-TR4 plasmids and then subcloned into pCDNA3-flag. All the constructions were verified by sequencing and/or Western blot analysis.

(9) RNA Interference

The pSuperior.retro.puro vector (OligoEngine) and lentivirus-based pLVTHM vector (Clontech, Palo Alto, Calif.) were used for the expression of shRNAs against TR4. TR4shRNA was generated by targeting a gene-specific sense sequence CGGGAGAAACCAAGCAATT (SEQ ID NO:8). The scramble control was constructed by targeting the sequence GTTCTCCGAACGTGTCACG (SEQ ID NO:9). The construction was confirmed by sequencing.

(10) Transfection, Virus Production, and Generation of Stable Cell Lines

For retrovirus mediated infection, phoenix cells were transfected with pSuperior.retro.puro-TR4-siRNA or its control scramble plasmids. To produce recombinant lentivirus, 293T cells were cotransfected with pLVTHM-TR4siRNA or its control scramble plasmid and lentivirus packaging plasmids using the Superfect method (Qiagen, Chatsworth, Calif.). At 48-72 h after transfection, infectious retrovirus or lentivirus were harvested and filtered through 0.45 M filter. The infection was carried out by adding the virus into the RAW264.7 cells or primary cultured mouse peritoneal macrophages. After 2 days transfection by Superfect or transduction, RAW264.7 cells were selected with 500 g/ml G418 for 10 days, or 5 g/ml puromycin for 3 days. The stable clones were confirmed by Western blot analysis.

(11) Electrophoretic Mobility Shift Assays (EMSA)

Nuclear extracts and EMSA were carried out as described previously (Yang et al. J Biol Chem, 2005). Briefly, 8 µg of nuclear extract protein was incubated in a reaction solution containing 20 mM Tris-HCl/pH 7.9, 2 mM MgCl$_2$, 1 mM EDTA, 50 mM KCl, 0.5 mM dithiothreitol, 10% glycerol, 0.1% Nonidet P-40, and 2 µg of poly(dI-dC). After 20 min, the $^{32}$P-end-labeled duplex oligonucleotide ($2\times10^4$ cpm) was added, and the reaction was incubated for another 20 min in ice. For antibody supershift analysis, 2 µg of anti-TR4 antibody was added to the reaction mixtures and incubated in ice for 20 min.

(12) Chromatin Immunoprecipitation Assay (ChIP)

The ChIP assays were performed as described previously (Yang et al. J Biol Chem, 2005). Cell lysates were precleared sequentially with normal mouse IgG and protein A-agarose. Anti-TR4 antibody (2.0 g) was added to the lysate and incubated at 4° C. overnight. For the negative control, IgG antibody was added in the sample. The primer pairs, which span the region of the CD36 promoter, were used for the amplification of PCR product.

(13) Statistical Analysis

The statistical analyses were performed using the Student's t-test. $P<0.05$ is considered significant.

G. SEQUENCES

G. Sequences

1. TR4
a) Protein id NP_003289 (SEQ ID NO: 2)

```
mtspspriqi istdsavasp qriqgsepas gplsvftsln
kekivtdqqt gqkiqivtav dasgspkqqf iltspdgagt
gkvilaspet ssakqliftt sdnlvpgriq ivtdsasver
llgktdvqrp qvveycvvcg dkasgrhyga vscegckgff
krsvrknlty scrsnqdcii nkhhrnrcqf crlkkclemg
mkmesvqser kpfdvqrekp sncaasteki yirkdlrspl
iatptfvadk dgarqtglld pgmlvniqqp liredgtvll
atdskaetsq galgtlanvv tslanlsesl nngdtseiqp
edqsaseitr afdtlakaln ttdssssps1 adgidtsggg
sihvisrdqs tpiievegpl lsdthvtfkl tmpspmpeyl
nvhyicesas rlllflsmhwa rsipafqalg qdcntslvra
cwnelftlgl aqcaqvmsls tilaaivnhl qnsiqedkls
gdrikqvmeh iwklqefcns makldidgye yaylkaivlf
spdhpgltst sqiekfqeka qmelqdyvqk tysedtyrla
rilvrlpalr lmssniteel fftglignvs idsiipyilk
metaeyngqi tgasl
``` b) Gene id NM_003298 (SEQ ID NO: 1)

```
ccgctcccac ctcggcgtct cgtctctcgc ccgctgcccc
gcgagcccgc ggcccccggg ctcccgccat ccgccgacac
cgggagcccg ggctcccgc gccctgccct ccgcgccggg
ggccgcccgc cgcagacacg ggaccgctt cgaggccgct
ttggcgccaa atcctgaggt aacacgtaca cagacctctc
ggccggaatc tccagggatg accagccct cccacgcat
ccagataatc tccaccgact ctgctgtagc ctcacctcag
cgcattcagg gctctgaacc tgcctctgcc ccattgagtg
ttttcacatc tttgaacaaa gagaagattg tcacagacca
gcagacagga cagaaaatcc agatagtcac cgcagtggac
gcctccggat cccccaaaca gcagttcatc ctgaccagcc
cagatggagc tggaactggg aaggtgatcc tggcttcccc
agagacatcc agcgccaagc aactcatatt caccacctca
gacaacctcg tccctggcag gatccagatt gtcacggatt
ctgcctctgt ggagcgttta ctggggaaga cggacgtcca
gcggccccag gtggtagagt actgtgtggt ctgtggcgac
aaagcctccg gccgtcacta tggggctgtc agttgtgaag
gttgcaaagg tttcttcaaa aggagtgtga ggaaaaattt
gacctacagc tgccggagca accaagactg catcatcaat
aaacatcacc ggaaccgctg tcagttttgc cggctgaaaa
aatgcttaga gatgggcatg aaaatggaat ctgtgcagag
tgaacggaag cccttcgatg tgcaacggga gaaaccaagc
aattgtgctg cttcaactga gaaaatctat atccggaaag
acctgagaag tccctgata gctactccca cgtttgtggc
agacaaagat ggagcaagac aaacaggtct tcttgatcca
gggatgcttg tgaacatcca gcagcctttg atacgtgagg
atggtacagt tctcctgcc acggattcta aggctgaaac
aagccaggga gctctgggca cactggcaaa tgtagtgacc
tcccttgcca acctaagtga atctttgaac aacggtgaca
cttcagaaat ccagccagag gaccagtctg caagtgagat
aactcgggca tttgatacct tagctaaagc acttaatacc
acagacagct cctcttctcc aagcttggca gatgggatag
acaccagtgg aggagggagc atccacgtca tcagcagaga
ccagtcgaca cccatcattg aggttgaagg ccccctcctt
tcagacacac acgtcacatt taagctaaca atgcccagtc
caatgccaga gtacctcaac gtgcactaca tctgtgagtc
tgcatcccgt ctgctttttcc tctcaatgca ctgggctcgg
```

-continued

```
tcaatcccag cctttcaggc acttgggcag gactgcaaca
ccagccttgt gcgggcctgc tggaatgagc tcttcaccct
cggcctggcc cagtgtgccc aggtcatgag tctctccacc
atcctggctg ccattgtcaa ccacctgcag aacagcatcc
aggaagataa acttttctgg gaccggataa agcaagtcat
ggagcacatc tggaagctgc aggagttctg taacagcatg
gcgaagctgg atatagatgg ctatgagtat gcataccttta
aagctatagt tctctttagc cccgatcatc caggtttgac
cagcacaagc cagattgaaa aattccaaga aaaggcacag
atggagttgc aggactatgt tcagaaaacc tactcagaag
acacctaccg attggcccgg atcctcgttc gcctgccggc
actcaggctg atgagctcca acataacaga agaacttttt
tttactggtc tcattggcaa tgtttcgata gacagcataa
tcccctacat cctcaagatg gagacagcag agtataatgg
ccagatcacc ggagccagtc tatagcgcaa accacacacc
tgccaaggag caacagaatc cttccaggac cgttcacata
caaagaaaag tagtggtatt ttggtatgtg caaatatttc
catatgttag ccatttcctg tctggtttct ccttatctgt
taatcccaga caatagcaat taaaagacta gtaggatcct
ttcctgacat aagaaatgtt ttaatgcctt ttgatgaagc
agcagatttt ggaacaatct tttaactcaa tttgtattta
gaaattctca aagggcaaaa aacaaaaaaa aaggtttat
aatgtcagaa actagtatta aagaaaactg aaagaacctg
agagaatagt atgtgtgtat atatatatat aaaaagtcc
ttggaattat agatactaat taccagggta ataatattag
cacttttctaa gcacttatca atgtgtaacg ttagcaacat
cttgcctgtg ggcagggcaa atggaaaact gtgtatgtct
tttgccgaaa tgctaatgat ttctgtgaaa actcactagg
gtacaggaga caatcattta tgtttaagaa aagaaggcat
cattcctaat tgtgtgcaca tgttgtggag ttgagctgaa
ttctgtgaat ggaaacgtgg ctcatttgca tcatgcagta
agtgggagtg tggtagcaca gtcggtggtg acccagttca
gaagcttcta gccatagagc agacacttgt caggttccct
gactacttgg tcctggtctc tgatgggcat ctgcagactc
ctctagaacc tgggggtctc cttttgatgac tggttatctg
aattggattg caactagtca gacattaact gccaaatgag
atgtacagtt cctccagcaa gtgaaaacat ccccaagtca
catccgccgc tcgtggcaga tggagccttg tgaccaaaaa
gtgcaaggtg ggcattttga gctcttgaca gtacttccaa
tacaattggg ggtgctgtg tgtttgtcca gatgggaggag
tgtggccttg gagtgtgagc gttaccttcc cagggctttc
cactccaaat gcccccttga aaagggctcg tgtttctgca
gctccatcat aactggtagg ctggattggg gctgggcagg
agcctgctgc cgcctggcga gagtggttag ggcctggtaa
agctggatgg aaggtttcag gacaatttct tcctgttgac
cttaaatacc agagattttta aaaatgtgta tagactcagc
atctctgttg gcaagtctgt taatgttacc agcacactgt
gcactttggt tccccccaggt gtgtgccagc cgaccacccc
ggagcatttt aaatgcaggc tgcttgctcc ttaaaaacaa
ccctcaattt ccagggtgat agtctttctc ctcataaatt
gtagcaacca gagtttacag caagaacagt atgcgcttaa
aaggaagtta tgtctaactt caaacacccg taaattccca
cggatgtgaa tatatagcaa gcttttcctg tttttgagaaca
gtggcatgtg gaagacccgg tcaattgctt tgtcttttgc
tttttaaata gtccagatta agaaaataca ccctgttggg
ttaaatttgc ctctcttgat ttgttaatca gatgatatcc
aaaaagatcc ctggacactc ccctgactca caggtgctct
gatctggctc aggctggcgc cacatgtgct ccacaggggt
gcagtctggc cagctacaga cgcccctgtg gtgccacatt
ggacagaatg gaagctgctg caggctcaag gcagaacagg
atgcttgatc ctgaagggtt agcagcactt tacgcaagtc
agtgttagta gggtaagtgg gaacagtgtt tccaacttct
aaattcttgt ttggatttaa ttatatcatt ttataattct
tgccttggca gcaaattttg gagagtagtg ggagtggcca
ttataaaatg atggaaagga tttaattttg ccagcttaaa
gtaattttta cttttctaac cctgatgtgt tttcagtttc
aaaattaaga caaaaaacca gctgagacaa tggaattagg
gcaggtttgt ttcatttctg ctttgtgaag cttttagtag
caggcatcct gcagctcagt ggtgcctcta acacagattg
ttgcctgcct tccgtcgttt tgatccttga gagtgaccat
gagggccatg ttgcagttcc ctgggaatac aagcataaca
gctttcagat cccagtcctt ggtgttgctg aaaaggtctc
caccagcccc tcctctcatt cccaggtcat tcagtggcag
ccagtaggct gcttagactc aggctggata aggaagtgtt
gggctgtggt gaaacaacct tgcagaaaac gtgattttgc
ttggaaaggt gctgattcta acctggtcct gctcttttag
tcccttgcct ggtgatggct gattccaggg actgttttgg
gctttgaaca cctcttggtt ggtttctgag atcctcttgg
ccttacttttg aagtggcctt ttcttttaagg atcatgtcca
cgtaacctgt attcttgctg ctttaactca tttcaagcct
ctgactgcag gtccatttca tctcctgtca ggttggttaa
gtaaagtcag cccaaagtca agaattactt aaagagatgc
aaaccaaata tttgggctcc aactttcaca gggcttatag
cccttattag cagtttgtga aactttgggt ttcatgaagt
gagacctgtc ctctggctac tgaactccat ggagccacgt
tcatgctccc tcttctactg gcctggctgc tcctccctca
atgaggagag gcagctggct cagagaggtg ggacagacac
atgctgtcat cagttaaggt agctctttt cagaagtatc
tcagataatg ttgggttaag acagatagat gttgaaaatg
gtggagatca ttacacatta gcataaaaca ggacaggaag
agatttttg aaagaccaaa ttagttgagc aagtaatact
tttcaagtta ctcctggaag gtgtttttaa ggaagtgtgt
tacctaccat actctcctaa tttgacattt ctgtgtcctg
aggagttaca tttattgtct aaccctttgcc ataaggctgt
ggtttgaggt tcttttgctg ttctgggctt tatatttaat
ttcaggtgta gtcacttcta agatgtgtaa ttgccctcaa
gagggactga tttttagctt gtcattgtca gtattgaatg
tggactcttc tgaggcagtt aggacaccag ccatggtgtt
aacagtggat gcgttaggct ccttaatctc aaggcaatat
ccacgctaca cacatactta ttagctgtct tacttgtttg
ggggatagtt acggcaagga gcaaaaaatt ctaaggactc
tagctgtttc tagtgctttt actttctcag tcctttgagg
acatttcctg cagacgcactc ttgctcacag cccgccctct
gcagggcttc cagcccctgg ccgcaatcac cagttcatgc
cacatgtgta catccatgtt ctgggacctg atctcattgg
agtccagaag cttgttgccc actttccagt gtaaatgact
ttatgtccaa tgggtgtcata ggtaacattt taactcttttt
cttagtccag gtcataggaa gtctcatcat ctgacagcca
ctttttctccc agggaaggcg gtgcccactg ggccctggga
atgcctgagc cagcagagca gatgcccac gtgcttcctt
tatccagctt ccattctctc agttatgagg ctctttgaaa
atgtcttaac tttgatgtaa attttaaag ccaaccccta
atcaagacag ggttggtttg ggtcttttgt acacagggtc
tggaccttct cattgtgtgc ctcccaccag cgtgcacttc
gtatgtccag ccctgggtcc cttcagcagc attgtgcgtg
tacaggtttc taggctgtaa gactgaatga atgtacatgt
gtttatatcc tctccatatg tacagtgtat atagtgtgtg
tatgtgtaca tagatgtata ttatgtatac agacatgtat
ccaaactttc cttttaaagag agttttttcat aaagttgcta
atgtaaactg atatgggtgt tccaaggtcc ctcggcaggg
aagatttgct ggtgattttc ttcactccat tttcctttgg
gtgagcctgc ctgggaaggg ccatgaagtc agaatctcca
ctctgcaaaa ggaagaattc caggcagaag aggttctgac
agggtgacat ttccgtatat tctctaggtt cggacaagag
ccaggaagct ggaagacagt ttatcttaat atccaaaact
aagtgggaat ttttaacctt ttcatgcacc tattcatggc
cctacctgga aggaacttgg cagttgggtt gagccatcag
ccttcccagc tctactcc tgttgagtag cccagagaca
ggcgtcacgg tcagagattc agaacggtct gtgtcagtga
ggcctgactc ccaaagatgg tagcaatttc ccaggcttgc
gctgtgctca gtcagcaaga tgtgggcac tgtcctatga
ctgaataaat agtaattccc atcttttctat cgccagttaa
aaataaacaa cctaccaagt attattcttt aaaactaagc
atggatgttg atggctaact tctgcggcat ataagctaca
gatctcaagt tacttctcta actgtaagca tgtaaatgac
tttaactcct ttctataagt tatgattta aattttcaga
taagaattgc attttaatat ggatatgtgt gcccttaaaa
gctacagata ccaaattttc ctcgtccagg tctactcgga
cgaattttcc cccttaatct ggccttaaac tgagactcgg
cccttgagag ccagggcctg gcccagcagt agttgctcat
agacctggga gcaggggcc tgggaaagg aatcactaga
ttgctgcaaa aactcacata atccacagtt tcctctttttt
cttttaaaa taagttatca aaatgtttta aaaacacttt
atgagaccat agtactcagt gccttttgtg agacagtggg
tcatttagcc ttcagcttcc ctgtttttgg tgtagagaaa
gcttctattt cactggcctc atcccacaag attgtgcgac
cttcccccgt catagcctgt cgtgacaatc acgctattga
aagtggcttt ctagttaaaa tgcaattgga aacttgacag
tctctaaatg aattaaaagt ttccttttggg gctatttagc
ttaacagcag tctcaaaata attaaagtgt gagcttaaga
aaagtatctt tgcggggaga aaaatgtcag atatttttaa
tgcccagcta taaataattt tggtgtcttg atatttatac
atgcaaaata aaaaaaat gttcaacatt tattgattga
tagactgtta aaatttaatg tttggaataa catttggaag
tagtagactt tgcattaaaa aatggctttt ctttaggaaa
gtataatcaa ttattttaat gaccatagca ttcatggact
caaatgctgc tgccacacac aactcaagtg ctgaatatt
tttctacagt ctctctgttc tacggattat cttgtaaacc
agtgttcaac tagtttttata actgaaaagc tgcacatttt
tcacagtaca agccgtagtt tttacctgta gtttggactt
ctctgttaga atgtaactgc attaccagcc ctttttaagg
catctatcta tcaaaggaaa atttgggtgt tagattttct
```

```
                          -continued
tgggaccgtt tctgtaacct ttgcccttca caatatagaa
aatattggtt ttgccattac attttaatgc caggtttaaa
acctgttgaa agctgcagct ttatacagct ttcttctccc
tgtgaaatca ctttgtttat gtgatggcat ttaaaaaata
gcatgttctt tttaaactga attttatatc taatcaatgt
cttcagtctt gaagaagaat ttgcattgtt gtgtttgtat
atagagtatt gcagtgcatg aattagcttt atgcatttta
ttaaatgctg tttcaatgtg gcattattgt tgtggcttaa
tactactacc taaatgaggt ttatactatt aaaagtgaat
taaagactaa 2. PPAR
a) Protein id NP_619726 (variant 1)
```

(SEQ ID NO: 3)

```
mtmvdtempf wptnfgissv dlsvmedhsh sfdikpfttv
dfssistphy edipftrtdp vvadykydlk lqeyqsaikv
epasppyyse ktqlynkphe epsnslmaie crvcgdkasg
fhygvhaceg ckgffrrtir lkliydrcdl ncrihkksrn
kcqycrfqkc lavgmshnai rfgrmpqaek ekllaeissd
idqlnpesad lralakhlyd syiksfpltk akarailtgk
ttdkspfviy dmnslmmged kikfkhitpl qeqskevair
ifqgcqfrsv eavqeiteya ksipgfvnld lndqvtllky
gvheiiytml aslmnkdgvl isegqgfmtr eflkslrkpf
gdfmepkfef avkfnaleld dsdlaifiav iilsgdrpgl
lnvkpiediq dnllqalelq lklnhpessq lfakllqkmt
dlrqivtehv qllqvikkte tdmslhpllq eiykdly
``` b) Gene id NM_138712 (variant 1)

(SEQ ID NO: 4)

```
ggcgcccgcg cccgccccg cgccgggccc ggctcggccc
gacccggctc cgccgcgggc aggcgggggcc cagcgcactc
ggagcccgga cccgagccgc agccgccgcc tggggcgctt
gggtcggcct cgaggacacc ggagaggggc gccacgccgc
cgtggccgca gatttgaaag aagccaacac taaaccacaa
atatacaaca aggccatttt ctcaaacgag agtcagcctt
taacgaaatg accatggttg acacagagat gccattctgg
cccaccaact ttgggatcag ctccgtggat ctctccgtaa
tggaagacca ctcccactcc tttgatatca agcccttcac
tactgttgac ttctccagca tttctactcc acattacgaa
gacattccat tcacaagaac agatccagtg gttgcagatt
acaagtatga cctgaaactt caagagtacc aaagtgcaat
caaagtggag cctgcatctc caccttatta ttctgagaag
actcagctct acaataagcc tcatgaagag ccttccaact
ccctcatggc aattgaatgt cgtgtctgtg gagataaagc
ttctggattt cactatggag ttcatgcttg tgaaggatgc
aagggtttct tccggagaac aatcagattg aagcttatct
atgacagatg tgatcttaac tgtcggatcc acaaaaaag
tagaaataaa tgtcagtact gtcggtttca gaaatgcctt
gcagtgggga tgtctcataa tgccatcagg tttgggcgga
tgccacaggc cgagaaggag aagctgttgg cggagatctc
cagtgatatc gaccagctga atccagagtc cgctgacctc
cgggcctgg caaaacattt gtatgactca tacataaagt
ccttcccgct gaccaaagca aaggcgaggg cgatcttgac
aggaaagaca acagacaaat caccattcgt tatctatgac
atgaattcct taatgatggg agaagataaa atcaagttca
aacacatcac ccccctgcag gagcagagca aagaggtggc
catccgcatc tttcagggct gccagtttcg ctccgtggag
gctgtgcagg agatcacaga gtatgccaaa agcattcctg
gttttgtaaa tcttgacttg aacgaccaag taactctcct
caaatatgga gtccacgaga tcatttacac aatgctggcc
tccttgatga ataaagatgg ggttctcata tccgagggcc
aaggcttcat gacaagggag tttctaaaga gcctgcgaaa
gccttttggt gactttatgg agcccaagtt tgagtttgct
gtgaagttca atgcactgga attagatgac agcgacttgg
caatatttat tgctgtcatt attctcagtg gagaccgccc
aggtttgctg aatgtgaagc ccattgaaga cattcaagac
aacctgctac aagccctgga gctccagctg aagctgaacc
acctgagtc ctcacagctg tttgccaagc tgctccagaa
aatgacagac ctcagacaga ttgtcacgga acacgtgcag
ctactgcagg tgatcaagaa gacggagaca gacatgagtc
ttcacccgct cctgcaggag atctacaagg acttgtacta
gcagagagtc ctgagccact gccaacattt cccttcttcc
agttgcacta ttctgaggga aaatctgaca cctaagaaat
ttactgtgaa aaagcatttt aaaaagaaaa ggttttagaa
tatgatctat tttatgcata ttgtttataa agacacattt
acaatttact tttaatatta aaaattacca tattatgaaa
ttgctgatag ta
```

PPAR response element A Consensus PPAR RE is TGAC-CTnTGACCT (SEQ ID NO:10) or AGGTCAnAG-GTCA (SEQ ID NO:11) which consists of direct repeats with various spacings separating them TR4 response element is also a direct repeat of AGGTCA (SEQ ID NO:12) with varying spacers separating the repeats. Many variations of the direct repeat can be response elements 5. pCMX-TR4 plasmids consist of the full length human TR4 gene subcloned into pCMX vector.

pCDNA3-flag TR4 is a derivative of Invitrogen's pCDNA3 vector comprising a synthetic linker containing a FLAG tag which consists of GACTACAAAGACGATGAC-GACAAG (SEQ ID NO:13). The full length human TR4 gene as referenced above was subcloned into pCDNA3-FLAG.

7. scramble control is a universal shRNA construct that is designed not to knockdown any gene's gene expression.

TR4 shRNA is an oligonucleotide that consists of the sense and antisense of a target sequence and also a hairpin consisting of CGGGAGAAACCAAGCAATTTCTCT-TGAAAATTGCTTGGTTTCT CCCG (SEQ ID NO:14). The oligonucleotide is then cloned into lentiviral or retroviral vectors to generate TR4 shRNA

H. REFERENCES

1. Glass C K & Witztum J L (2001) Atherosclerosis. the road ahead. (Translated from eng) *Cell* 104(4):503-516 (in eng).
2. Endemann G, et al. (1993) CD36 is a receptor for oxidized low density lipoprotein. (Translated from eng) *J Biol Chem* 268(16):11811-11816 (in eng).
3. Kodama T, Reddy P, Kishimoto C, & Krieger M (1988) Purification and characterization of a bovine acetyl low density lipoprotein receptor. (Translated from eng) *Proc Natl Acad Sci USA* 85(23):9238-9242 (in eng).
4. Febbraio M, et al. (1999) A null mutation in murine CD36 reveals an important role in fatty acid and lipoprotein metabolism. (Translated from eng) *J Biol Chem* 274(27): 19055-19062 (in eng).
5. Kunjathoor V V, et al. (2002) Scavenger receptors class A-I/II and CD36 are the principal receptors responsible for the uptake of modified low density lipoprotein leading to lipid loading in macrophages. (Translated from eng) *J Biol Chem* 277(51):49982-49988 (in eng).
6. Suzuki H, et al. (1997) A role for macrophage scavenger receptors in atherosclerosis and susceptibility to infection. (Translated from eng) *Nature* 386(6622):292-296 (in eng).
7. Febbraio M, et al. (2000) Targeted disruption of the class B scavenger receptor CD36 protects against atherosclerotic lesion development in mice. (Translated from eng) *J Clin Invest* 105(8):1049-1056 (in eng).
8. Rahaman S O, et al. (2006) A CD36-dependent signaling cascade is necessary for macrophage foam cell formation. (Translated from eng) *Cell Metab* 4(3):211-221 (in eng).
9. Babaev V R, et al. (2000) Reduced atherosclerotic lesions in mice deficient for total or macrophage-specific expression of scavenger receptor-A. (Translated from eng) *Arterioscler Thromb Vasc Biol* 20(12):2593-2599 (in eng).
10. Witztum J L (2005) You are right too! (Translated from eng) *J Clin Invest* 115(8):2072-2075 (in eng).
11. van Berkel T J, et al. (2005) Scavenger receptors: friend or foe in atherosclerosis? (Translated from eng) *Curr Opin Lipidol* 16(5):525-535 (in eng).
12. Moore K J, et al. (2005) Loss of receptor-mediated lipid uptake via scavenger receptor A or CD36 pathways does not ameliorate atherosclerosis in hyperlipidemic mice. (Translated from eng) *J Clin Invest* 115(8):2192-2201 (in eng).
13. Kliewer S A, Lehmann J M, & Willson T M (1999) Orphan nuclear receptors: shifting endocrinology into reverse. (Translated from eng) *Science* 284(5415):757-760 (in eng).
14. Nagy L, Tontonoz P, Alvarez J G, Chen H, & Evans R M (1998) Oxidized LDL regulates macrophage gene expression through ligand activation of PPARgamma (Translated from eng) *Cell* 93(2):229-240 (in eng).
15. Kliewer S A, et al. (1995) A prostaglandin J2 metabolite binds peroxisome proliferator-activated receptor gamma and promotes adipocyte differentiation. (Translated from eng) *Cell* 83(5):813-819 (in eng).
16. Forman B M, et al. (1995) 15-Deoxy-delta 12,14-prostaglandin J2 is a ligand for the adipocyte determination factor PPAR gamma. (Translated from eng) *Cell* 83(5): 803-812 (in eng).
17. Tontonoz P, Hu E, & Spiegelman B M (1995) Regulation of adipocyte gene expression and differentiation by peroxisome proliferator activated receptor gamma (Translated from eng) *Curr Opin Genet Dev* 5(5):571-576 (in eng).
18. Lehmann J M, et al. (1995) An antidiabetic thiazolidinedione is a high affinity ligand for peroxisome proliferator-activated receptor gamma (PPAR gamma). (Translated from eng) *J Biol Chem* 270(22):12953-12956 (in eng).
19. Tontonoz P, Nagy L, Alvarez J G, Thomazy V A, & Evans R M (1998) PPARgamma promotes monocyte/macrophage differentiation and uptake of oxidized LDL. (Translated from eng) *Cell* 93(2):241-252 (in eng).
20. Lee Y F, Lee H J, & Chang C (2002) Recent advances in the TR2 and TR4 orphan receptors of the nuclear receptor superfamily. (Translated from eng) *J Steroid Biochem Mol Biol* 81(4-5):291-308 (in eng).
21. Yang X, et al. (2006) Nuclear receptor expression links the circadian clock to metabolism. (Translated from eng) *Cell* 126(4):801-810 (in eng).
22. Bookout A L, et al. (2006) Anatomical profiling of nuclear receptor expression reveals a hierarchical transcriptional network. (Translated from eng) *Cell* 126(4):789-799 (in eng).
23. Collins L L, et al. (2004) Growth retardation and abnormal maternal behavior in mice lacking testicular orphan nuclear receptor 4. (Translated from eng) *Proc Natl Acad Sci USA* 101(42):15058-15063 (in eng).
24. Chen Y T, Collins L L, Uno H, & Chang C (2005) Deficits in motor coordination with aberrant cerebellar development in mice lacking testicular orphan nuclear receptor 4. (Translated from eng) *Mol Cell Biol* 25(7):2722-2732 (in eng).
25. Mu X, et al. (2004) Targeted inactivation of testicular nuclear orphan receptor 4 delays and disrupts late meiotic prophase and subsequent meiotic divisions of spermatogenesis. (Translated from eng) *Mol Cell Biol* 24(13):5887-5899 (in eng).
26. Zhang Y, et al. (2007) Loss of Testicular Orphan Receptor 4 Impairs Normal Myelination in Mouse Forebrain. (Translated from Eng) *Mol Endocrinol* (in Eng).
27. Liu N C, et al. (2007) Loss of TR4 orphan nuclear receptor reduces phosphoenolpyruvate carboxykinase-mediated gluconeogenesis. (Translated from eng) *Diabetes* 56(12): 2901-2909 (in eng).
28. Schote A B, Turner J D, Schiltz J, & Muller C P (2007) Nuclear receptors in human immune cells: expression and correlations. (Translated from eng) *Mol Immunol* 44(6): 1436-1445 (in eng).
29. Barish G D, et al. (2005) A Nuclear Receptor Atlas: macrophage activation. (Translated from eng) *Mol Endocrinol* 19(10):2466-2477 (in eng).
30. Forman B M, Chen J, & Evans R M (1997) Hypolipidemic drugs, polyunsaturated fatty acids, and eicosanoids are ligands for peroxisome proliferator-activated receptors alpha and delta. (Translated from eng) *Proc Natl Acad Sci USA* 94(9):4312-4317 (in eng).
31. Kliewer S A, et al. (1997) Fatty acids and eicosanoids regulate gene expression through direct interactions with peroxisome proliferator-activated receptors alpha and gamma (Translated from eng) *Proc Natl Acad Sci USA* 94(9):4318-4323 (in eng).
32. Xu H E, et al. (1999) Molecular recognition of fatty acids by peroxisome proliferator-activated receptors. (Translated from eng) *Mol Cell* 3(3):397-403 (in eng).
33. Castrillo A & Tontonoz P (2004) PPARs in atherosclerosis: the clot thickens. (Translated from eng) *J Clin Invest* 114(11):1538-1540 (in eng).
34. Joseph S B & Tontonoz P (2003) LXRs: new therapeutic targets in atherosclerosis? (Translated from eng) *Curr Opin Pharmacol* 3(2):192-197 (in eng).
35. Beaven S W & Tontonoz P (2006) Nuclear receptors in lipid metabolism: targeting the heart of dyslipidemia. (Translated from eng) *Annu Rev Med* 57:313-329 (in eng).
36. Li A C, et al. (2000) Peroxisome proliferator-activated receptor gamma ligands inhibit development of atherosclerosis in LDL receptor-deficient mice. (Translated from eng) *J Clin Invest* 106(4):523-531 (in eng).
37. Ricote M, Li A C, Willson T M, Kelly C J, & Glass C K (1998) The peroxisome proliferator-activated receptor-gamma is a negative regulator of macrophage activation. (Translated from eng) *Nature* 391(6662):79-82 (in eng).
38. Nissen S E & Wolski K (2007) Effect of rosiglitazone on the risk of myocardial infarction and death from cardiovascular causes. (Translated from eng) *N Engl J Med* 356(24): 2457-2471 (in eng).
39. Yki-Jarvinen H (2004) Thiazolidinediones. (Translated from eng) *N Engl J Med* 351(11):1106-1118 (in eng).
40. Palinski W, et al. (1994) ApoE-deficient mice are a model of lipoprotein oxidation in atherogenesis. Demonstration of oxidation-specific epitopes in lesions and high titers of autoantibodies to malondialdehyde-lysine in serum. (Translated from eng) *Arterioscler Thromb* 14(4):605-616 (in eng).
41. Lehr H A, et al. (2001) Immunopathogenesis of atherosclerosis: endotoxin accelerates atherosclerosis in rabbits on hypercholesterolemic diet. (Translated from eng) *Circulation* 104(8):914-920 (in eng).
42. Wang H, Berschneider H M, Du J, & Black D D (1997) Apolipoprotein secretion and lipid synthesis: regulation by fatty acids in newborn swine intestinal epithelial cells. (Translated from eng) *Am J Physiol* 272(5 Pt 1):G935-942 (in eng).
43. Yang L, et al. (2004) Androgen suppresses PML protein expression in prostate cancer CWR22R cells. (Translated from eng) *Biochem Biophys Res Commun* 314(1):69-75 (in eng).
44. Xie S, et al. (2004) Regulation of interleukin-6-mediated PI3K activation and neuroendocrine differentiation by androgen signaling in prostate cancer LNCaP cells. (Translated from eng) *Prostate* 60(1):61-67 (in eng).
45. Yang L, et al. (2005) Induction of androgen receptor expression by phosphatidylinositol 3-kinase/Akt downstream substrate, FOXO3a, and their roles in apoptosis of LNCaP prostate cancer cells. (Translated from eng) *J Biol Chem* 280(39):33558-33565 (in eng).

What is claimed is:

1. A method of isolating drug candidates that do not bind TR4 and bind PPAR comprising:
   a. incubating drug candidates with TR4;
   b. isolating drug candidates that do not bind TR4;
   c. incubating the TR4 non-binding drug candidates with PPAR; and
   d. isolating the TR4 non-binding drug candidates that bind PPAR.

2. The method of claim 1 wherein incubating the drug candidates with TR4, comprises combining drug candidates and TR4 in a mixture allowing for contact between the drug candidates and TR4.

3. The method of claim 1 wherein isolating drug candidates that do not bind TR4 comprises:
   passing the drug candidates over a TR4 linked to a support.

4. The method of claim 3 wherein the support linked to TR4 comprises sepharose, an agarose bead or an antibody.

5. The method of claim 3 wherein the linked TR4 comprises a covalent bond between the support and TR4.

6. The method of claim 3 wherein the linked TR4 comprises a non-covalent bond between the support and TR4.

7. The method of claim 1 wherein isolating the drug candidates that bind PPAR comprises:
   a. passing the TR4 non-binding drug candidates over PPAR linked to a support; and
   b. eluting the drug candidates bound to the linked PPAR.

8. The method of claim 7 wherein the support linked to TR4 comprises sepharose, agarose beads or antibodies.

9. The method of claim 7 wherein the linked PPAR comprises a covalent bond between the support and PPAR.

10. The method of claim 7 wherein the linked PPAR comprises a non-covalent bond between the support and PPAR.

11. The method of claim 7 wherein eluting the drug candidates bound to linked PPAR comprises: washing the linked PPAR with a wash comprising an elution molecule; washing the linked PPAR with a wash comprising a low or high pH buffer; or washing the linked PPAR with a wash comprising a detergent.

12. The method of claim 11 wherein the elution molecule is a polyunsaturated fatty acid (PUFA).

13. The method of claim 12, wherein the PUFA comprises an omega-3 fatty acid.

14. A method of isolating drug candidates that do not bind PPAR and bind TR4 comprising:
   a. incubating drug candidates with PPAR;
   b. isolating drug candidates that do not bind PPAR;
   c. incubating the PPAR non-binding drug candidates with TR4; and
   d. isolating the PPAR non-binding drug candidates that bind TR4.

15. The method of claim 14 wherein incubating the drug candidates with PPAR, comprises combining drug candidates and PPAR in a mixture allowing for contact between the drug candidates and PPAR.

16. The method of claim 14 wherein isolating drug candidates that do not bind PPAR comprises:
   passing the drug candidates over PPAR linked to a support.

17. The method of claim 16 wherein the support linked to PPAR comprises sepharose, an agarose bead or an antibody.

18. The method of claim 16 wherein the linked PPAR comprises a covalent bond between the support and PPAR.

19. The method of claim 16 wherein the linked PPAR comprises a non-covalent bond between the support and PPAR.

20. The method of claim 14 wherein isolating the drug candidates that bind TR4 comprises:
   a. passing the PPAR non-binding drug candidates over TR4 linked to a support; and
   b. eluting the drug candidates bound to the linked TR4.

21. The method of claim 20, wherein the support linked to PPAR comprises sepharose, agarose beads or antibodies.

22. The method of claim 20, wherein the linked TR4 comprises a covalent bond between the support and TR4.

23. The method of claim 20 wherein the linked TR4 comprises a non-covalent bond between the support and TR4.

24. The method of claim 20 wherein eluting the drug candidates bound to linked TR4 comprises: washing the linked TR4 with a wash comprising an elution molecule; washing the linked TR4 with a wash comprising a low or high pH buffer; or washing the linked TR4 with a wash comprising a detergent.

25. The method of claim 24 wherein the elution molecule comprises an omega-3 fatty acid.

26. The method of claim 1, wherein the drug candidates are drugs or small molecules.

27. The method of claim 14, wherein the drug candidates are drugs or small molecules.

* * * * *